(12) United States Patent
Bharadwaj et al.

(10) Patent No.: US 10,643,371 B2
(45) Date of Patent: May 5, 2020

(54) TREATMENT PROCEDURE PLANNING SYSTEM AND METHOD

(71) Applicant: COVIDIEN LP, Mansfield, MA (US)

(72) Inventors: Jeetendra Bharadwaj, Superior, CO (US); Kevin J. Frank, Lafayette, CO (US); Darren G. Girotto, Louisville, CO (US); Benjamin M. Corum, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 389 days.

(21) Appl. No.: 14/821,912

(22) Filed: Aug. 10, 2015

(65) Prior Publication Data
US 2016/0038247 A1    Feb. 11, 2016

Related U.S. Application Data

(60) Provisional application No. 62/035,863, filed on Aug. 11, 2014, provisional application No. 62/035,851, filed on Aug. 11, 2014.

(51) Int. Cl.
*G06T 15/08* (2011.01)
*A61B 90/10* (2016.01)
(Continued)

(52) U.S. Cl.
CPC .............. *G06T 15/08* (2013.01); *A61B 6/032* (2013.01); *A61B 34/10* (2016.02); *A61B 90/10* (2016.02);
(Continued)

(58) Field of Classification Search
CPC .............. G06F 3/0481; G06F 3/04842; G06F 3/04847; G06T 15/08; G06T 19/00;
(Continued)

(56) References Cited

U.S. PATENT DOCUMENTS 5,611,025 A    3/1997  Lorensen et al.
5,699,799 A   12/1997  Xu et al.
(Continued)

FOREIGN PATENT DOCUMENTS

EP    2744438 B1     6/2014
JP    2007267773 A  10/2007
(Continued)

OTHER PUBLICATIONS

Reitinger, B. et al., "Spatial Analysis Tools for Virtual Reality-based Surgical Planning", Virtual Reality, 2006, pp. 37-45.
(Continued)

*Primary Examiner* — Katherine L Fernandez
*Assistant Examiner* — Yi-Shan Yang

(57) ABSTRACT

A system and method for planning surgical procedure including a treatment zone setting view presenting at least one slice of a 3D reconstruction generated from CT image data including a target. The treatment zone setting view presenting a treatment zone marker defining a location and a size of a treatment zone and configured to adjust the treatment zone marker in response to a received user input. The system and method further including a volumetric view presenting a 3D volume derived from the 3D reconstruction and a 3D representation of the treatment zone marker relative to structures depicted in the 3D volume.

16 Claims, 19 Drawing Sheets

(51) Int. Cl.
- *G06T 19/00* (2011.01)
- *A61B 34/10* (2016.01)
- *A61B 6/03* (2006.01)
- *G06F 3/0481* (2013.01)
- *G06F 3/0484* (2013.01)
- *G06T 7/00* (2017.01)
- *A61B 6/00* (2006.01)
- *A61B 6/12* (2006.01)
- *A61N 5/10* (2006.01)
- *A61B 34/00* (2016.01)
- *A61B 18/00* (2006.01)

(52) U.S. Cl.
CPC ........ *G06F 3/0481* (2013.01); *G06F 3/04842* (2013.01); *G06F 3/04847* (2013.01); *G06T 7/0012* (2013.01); *G06T 19/00* (2013.01); *A61B 6/12* (2013.01); *A61B 6/463* (2013.01); *A61B 6/465* (2013.01); *A61B 6/469* (2013.01); *A61B 6/487* (2013.01); *A61B 6/5235* (2013.01); *A61B 34/25* (2016.02); *A61B 2018/00577* (2013.01); *A61B 2034/101* (2016.02); *A61B 2034/102* (2016.02); *A61B 2034/105* (2016.02); *A61B 2034/107* (2016.02); *A61B 2560/0475* (2013.01); *A61B 2576/00* (2013.01); *A61N 5/1001* (2013.01); *A61N 5/103* (2013.01); *A61N 2005/1074* (2013.01); *G06T 2200/24* (2013.01); *G06T 2207/10081* (2013.01); *G06T 2207/20108* (2013.01); *G06T 2210/41* (2013.01); *G06T 2219/028* (2013.01)

(58) Field of Classification Search
CPC ....... G06T 2200/24; G06T 2207/10081; G06T 2207/20108; G06T 2210/41; G06T 2219/028; A61B 19/20; A61B 19/50; A61B 19/56; A61B 2019/502; A61B 2019/505; A61B 2019/507; A61B 2019/524; A61B 2019/5265; A61B 2019/5466; A61B 2019/5483; A61B 2560/0475; A61B 6/032; A61B 6/12; A61B 6/463; A61B 6/465; A61B 6/469; A61B 6/487; A61B 6/5235

See application file for complete search history.

(56) References Cited

U.S. PATENT DOCUMENTS

| | | |
|---|---|---|
| 5,782,762 A | 7/1998 | Vining |
| 5,881,124 A | 3/1999 | Giger et al. |
| 5,891,030 A | 4/1999 | Johnson et al. |
| 5,920,319 A | 7/1999 | Vining et al. |
| 5,971,767 A | 10/1999 | Kaufman et al. |
| 6,047,080 A | 4/2000 | Chen et al. |
| 6,064,904 A * | 5/2000 | Yanof .................. A61B 90/10 600/414 |
| 6,083,162 A | 7/2000 | Vining |
| 6,138,045 A | 10/2000 | Kupinski et al. |
| 6,151,404 A | 11/2000 | Pieper |
| 6,161,034 A | 12/2000 | Burbank et al. |
| 6,181,348 B1 | 1/2001 | Geiger |
| 6,183,497 B1 | 2/2001 | Sing et al. |
| 6,246,784 B1 | 6/2001 | Summers et al. |
| 6,270,464 B1 | 8/2001 | Fulton, III et al. |
| 6,332,089 B1 | 12/2001 | Acker et al. |
| 6,347,241 B2 | 2/2002 | Burbank et al. |
| 6,350,244 B1 | 2/2002 | Fisher |
| 6,356,782 B1 | 3/2002 | Sirimanne et al. |
| 6,366,800 B1 | 4/2002 | Vining et al. |
| 6,427,081 B1 | 7/2002 | Burbank et al. |
| 6,450,937 B1 | 9/2002 | Mercereau et al. |
| 6,496,188 B1 | 12/2002 | Deschamps et al. |
| 6,501,848 B1 | 12/2002 | Carroll et al. |
| 6,505,065 B1 | 1/2003 | Yanof et al. |
| 6,506,065 B1 | 1/2003 | Castleman |
| 6,526,162 B2 | 2/2003 | Asano et al. |
| 6,603,868 B1 | 8/2003 | Ludwig et al. |
| 6,605,294 B2 | 8/2003 | Sawhney |
| 6,694,163 B1 | 2/2004 | Vining |
| 6,699,205 B2 | 3/2004 | Fulton, III et al. |
| 6,730,042 B2 | 5/2004 | Fulton et al. |
| 6,829,379 B1 | 12/2004 | Knoplioch et al. |
| 6,898,263 B2 | 5/2005 | Avinash et al. |
| 6,909,913 B2 | 6/2005 | Vining |
| 6,925,200 B2 | 8/2005 | Wood et al. |
| 6,993,375 B2 | 1/2006 | Burbank et al. |
| 6,996,433 B2 | 2/2006 | Burbank et al. |
| 7,006,677 B2 | 2/2006 | Manjeshwar et al. |
| 7,072,501 B2 | 7/2006 | Wood et al. |
| 7,083,578 B2 | 8/2006 | Lewkowicz et al. |
| 7,149,564 B2 | 12/2006 | Vining et al. |
| 7,167,180 B1 | 1/2007 | Shibolet |
| 7,179,220 B2 | 2/2007 | Kukuk |
| 7,201,762 B2 | 4/2007 | Greene, Jr. et al. |
| 7,229,417 B2 | 6/2007 | Foerster et al. |
| 7,236,558 B2 | 6/2007 | Saito et al. |
| 7,315,639 B2 | 1/2008 | Kuhnigk |
| 7,324,104 B1 | 1/2008 | Bitter et al. |
| 7,329,414 B2 | 2/2008 | Fisher et al. |
| 7,332,566 B2 | 2/2008 | Pathak et al. |
| 7,336,809 B2 | 2/2008 | Zeng et al. |
| 7,397,937 B2 | 7/2008 | Schneider et al. |
| 7,428,334 B2 | 9/2008 | Schoisswohl et al. |
| 7,452,357 B2 | 11/2008 | Vlegele et al. |
| 7,517,320 B2 | 4/2009 | Wibowo et al. |
| 7,518,619 B2 | 4/2009 | Stoval, III et al. |
| 7,565,191 B2 | 7/2009 | Burbank et al. |
| 7,592,418 B2 | 9/2009 | Pathak et al. |
| 7,618,567 B2 | 11/2009 | Chi Sing et al. |
| 7,625,397 B2 | 12/2009 | Foerster et al. |
| 7,668,582 B2 | 2/2010 | Sirimanne et al. |
| 7,702,153 B2 | 4/2010 | Hong et al. |
| 7,702,378 B2 | 4/2010 | Bolan et al. |
| 7,756,316 B2 | 7/2010 | Odry et al. |
| 7,792,565 B2 | 9/2010 | Vining |
| 7,809,176 B2 | 10/2010 | Gundel |
| 7,822,461 B2 | 10/2010 | Geiger et al. |
| 7,901,348 B2 | 3/2011 | Soper et al. |
| 7,907,772 B2 | 3/2011 | Wang et al. |
| 7,929,014 B2 | 4/2011 | Akimoto et al. |
| 7,972,619 B2 | 7/2011 | Fisher |
| 7,985,187 B2 | 7/2011 | Wibowo et al. |
| 8,009,891 B2 | 8/2011 | de Vaan |
| 8,049,777 B2 | 11/2011 | Akimoto et al. |
| 8,079,964 B2 | 12/2011 | Reichel et al. |
| 8,157,862 B2 | 4/2012 | Corbitt, Jr. |
| 8,170,328 B2 | 5/2012 | Masumoto et al. |
| 8,199,981 B2 | 6/2012 | Koptenko et al. |
| 8,208,708 B2 | 6/2012 | Homan et al. |
| 8,224,424 B2 | 7/2012 | Burbank et al. |
| 8,267,927 B2 | 9/2012 | Dalal et al. |
| 8,280,486 B2 | 10/2012 | Miller et al. |
| 8,292,822 B2 | 10/2012 | Fulton et al. |
| 8,306,602 B2 | 11/2012 | Sirimanne et al. |
| 8,417,009 B2 | 4/2013 | Mizuno |
| 8,509,877 B2 | 8/2013 | Mori et al. |
| 8,670,816 B2 * | 3/2014 | Green .................. A61B 8/0841 600/424 |
| 8,682,045 B2 | 3/2014 | Vining et al. |
| 8,698,806 B2 | 4/2014 | Kunert et al. |
| 8,730,237 B2 | 5/2014 | Ruijters et al. |
| 8,768,029 B2 | 7/2014 | Helm et al. |
| 8,798,227 B2 | 8/2014 | Tsukagoshi et al. |
| 8,798,339 B2 | 8/2014 | Mielekamp et al. |
| 8,819,591 B2 | 8/2014 | Wang et al. |
| 2004/0246269 A1 * | 12/2004 | Serra .................. G06F 3/0481 345/619 |
| 2005/0215854 A1 * | 9/2005 | Ozaki ............... A61B 1/00009 600/109 |

(56) References Cited

U.S. PATENT DOCUMENTS

| | | | |
|---|---|---|---|
| 2006/0149147 A1* | 7/2006 | Yanof | A61B 6/12 600/424 |
| 2008/0123922 A1 | 5/2008 | Gielen et al. | |
| 2008/0183073 A1 | 7/2008 | Higgins et al. | |
| 2009/0088635 A1 | 4/2009 | Fisher | |
| 2009/0312629 A1* | 12/2009 | Razzaque | A61B 5/06 600/426 |
| 2010/0029908 A1 | 2/2010 | Sing et al. | |
| 2010/0113920 A1 | 5/2010 | Foerster et al. | |
| 2010/0228534 A1 | 9/2010 | Gilboa et al. | |
| 2010/0310146 A1 | 12/2010 | Higgins et al. | |
| 2011/0251607 A1 | 10/2011 | Kruecker et al. | |
| 2012/0050258 A1* | 3/2012 | Kay | G06F 3/0425 345/419 |
| 2012/0200560 A1* | 8/2012 | Masumoto | G06T 19/20 345/419 |
| 2012/0203065 A1 | 8/2012 | Higgins et al. | |
| 2012/0215096 A1* | 8/2012 | Gilboa | G09B 23/28 600/424 |
| 2012/0249546 A1 | 10/2012 | Tschirren et al. | |
| 2012/0280135 A1 | 11/2012 | Bal | |
| 2012/0287238 A1 | 11/2012 | Onishi et al. | |
| 2013/0197357 A1* | 8/2013 | Green | A61B 8/0841 600/424 |
| 2013/0317363 A1* | 11/2013 | Case | A61B 8/565 600/439 |
| 2014/0201669 A1 | 7/2014 | Liu et al. | |
| 2014/0228835 A1* | 8/2014 | Mielekamp | A61B 34/25 606/34 |
| 2014/0344742 A1* | 11/2014 | Wiemker | G06T 19/003 715/771 |

FOREIGN PATENT DOCUMENTS

| | | |
|---|---|---|
| WO | 02064011 A2 | 8/2002 |
| WO | 2004110242 A2 | 12/2004 |

OTHER PUBLICATIONS

Extended European Search Report issued in Appl. No. EP 15831473.2 dated Apr. 20, 2018.

Australian Examination Report No. 1 issued in corresponding Appl. No. AU 2015301863 dated Apr. 26, 2019 (3 pages).

Office Action issued in corresponding Japanese Appl. No. 2017-507402 dated Sep. 10, 2019, together with English language translation (15 pages).

Office Action issued in corresponding Chinese Appl. No. CN 201580049552.4 dated Sep. 4, 2019 (8 pages).

* cited by examiner

TREATMENT PROCEDURE PLANNING SYSTEM AND METHOD

CROSS-REFERENCE TO RELATED APPLICATIONS

This application claims the benefit of, and priority to, U.S. Provisional Patent Application Nos. 62/035,863 and 62/035,851, both of which were filed on Aug. 11, 2014. This application is related to U.S. patent application Ser. No. 14/821,950, filed on Aug. 10, 2015. The entire contents of each of the above applications are hereby incorporated herein by reference.

BACKGROUND

1. Technical Field

The present disclosure relates to a system and method for planning a treatment procedure.

2. Discussion of Related Art

When planning a treatment procedure, clinicians often rely on patient data including X-ray data, computed tomography (CT) scan data, magnetic resonance imaging (MRI) data, or other imaging data that allows the clinician to view the internal anatomy of a patient. The clinician utilizes the patient data to identify targets of interest and to develop strategies for accessing the targets of interest for the surgical procedure.

The use of CT images as a diagnostic tool has become routine and CT results are frequently the primary source of information available to a clinician regarding the size and location of a lesion, tumor or other similar target of interest. This information is used by the clinician for planning an operative procedure such as a biopsy or an ablation procedure, but is only available as "offline" information which must typically be memorized to the best of the practitioner's ability prior to beginning a procedure. CT images are typically obtained by digitally imaging a patient in slices in each of the axial, coronal and sagittal directions. A clinician reviews the CT image data slice by slice from each direction when attempting to identify or locate a target. It is often difficult, however, for the clinician to effectively plan a surgical ablation procedure based on the X-rays, CT images, or MRIs in their raw form.

SUMMARY

Systems and methods for planning a treatment procedure are provided.

In an aspect of the present disclosure, a system for planning a treatment procedure is disclosed including a computing device having a memory and at least one processor and a program stored in the memory that, when executed by the processor, presents a user interface that guides a user through the planning of a treatment procedure. The user interface includes a target selection view presenting a slice of a 3D reconstruction generated from CT image data of a patient. The target selection view is configured to select at least one target anatomical feature from the presented slice in response to a received user input. The user interface further includes a treatment zone setting view presenting at least one slice of the 3D reconstruction including the target anatomical feature. The treatment zone setting view further presents a treatment zone marker defining a location and a size of a treatment zone. The treatment zone setting view is configured to adjust the treatment zone marker in response to a received user input. The user interface further includes an access route setting view configured to set an access route to the treatment zone in response to a received user input and a review view configured to present a three-dimensional model of the treatment zone and the access route.

In another aspect of the present disclosure, one or more of the treatment zone setting view, access route setting view, and review view are presented separately.

In a further aspect of the present disclosure, at least one dimension of the treatment zone marker is adjustable in response to a received user input to adjust the size of the treatment zone.

In a further aspect of the present disclosure, the treatment zone setting view presents each of an axial slice of the 3D reconstruction, a coronal slice of the 3D reconstruction and a sagittal slice of the 3D reconstruction. In an aspect of the present disclosure, the adjustment of the at least one dimension of the treatment zone marker in response to the received user input in one of the axial, coronal, and sagittal slices adjusts at least one dimension of the treatment zone marker in at least one other of the axial, coronal, and sagittal slices.

In yet another aspect of the present disclosure, the treatment zone setting view further presents at least one treatment parameter value. The at least one treatment parameter value is adjustable in response to a received user input.

In a further aspect of the present disclosure, the at least one treatment parameter value is selected from the group consisting of a power setting, a duration setting, an instrument type, and a size of the treatment zone.

In another aspect of the present disclosure, adjusting the at least one treatment parameter value automatically adjusts at least one other treatment parameter value.

In an aspect of the present disclosure, the treatment zone is presented in the three-dimensional model as a three-dimensional treatment volume.

In an aspect of the present disclosure, a non-transitory computer-readable storage medium is disclosed that is encoded with a program that, when executed by a processor, causes the processor to perform the steps of importing CT image data of a patient, generating a 3D reconstruction from the CT image data, presenting a slice of the 3D reconstruction, selecting a target anatomical feature from the slice of the 3D reconstruction in response to a received user input, setting a treatment zone in response to a received user input including presenting at least one slice of the 3D reconstruction including the target anatomical feature and presenting a treatment zone marker defining a location and a size of the treatment zone on the presented at least one slice of the 3D reconstruction, setting an access route to the treatment zone in response to a received user input, and presenting a three-dimensional model including the treatment zone and the access route.

In another aspect of the present disclosure, the setting of the treatment zone includes adjusting at least one dimension of the treatment zone marker to adjust the size of the treatment zone.

In yet another aspect of the present disclosure, the treatment zone marker is presented in each of an axial slice of the 3D reconstruction, a coronal slice of the 3D reconstruction, and a sagittal slice of the 3D reconstruction. In a further aspect of the present disclosure, adjustment of the at least one dimension of the treatment zone marker in one of the axial, coronal, and sagittal slices automatically adjusts at least one dimension of the treatment zone marker in at least one other of the axial, coronal, and sagittal slices.

In another aspect of the present disclosure, setting the treatment zone further includes presenting at least one treatment parameter value, and adjusting the at least one treatment parameter value.

In a further aspect of the present disclosure, the at least one treatment parameter value is selected from the group consisting of a power setting, a duration setting, and instrument type, and a size of the treatment zone.

In yet a further aspect of the present disclosure, adjusting the at least one treatment parameter value automatically adjusts at least one other treatment parameter value of the treatment zone.

In another aspect of the present disclosure, the treatment zone is presented in the three-dimensional model as a three-dimensional treatment volume.

In an aspect of the present disclosure, a system for planning a treatment procedure is disclosed. The system includes a computing device having a memory and at least one processor, and a program stored in the memory that, when executed by the processor, presents a user interface that guides a user through the planning of the treatment procedure. The user interface includes a treatment zone setting view presenting at least one slice of a 3D reconstruction generated from CT image data including a target. The treatment zone setting view further presents a treatment zone marker defining a location and a size of a treatment zone and is configured to adjust the treatment zone marker in response to a received user input. The user interface further includes a volumetric view presenting a 3D volume derived from the 3D reconstruction and a 3D representation of the treatment zone marker relative to structures depicted in the 3D volume.

In another aspect of the present disclosure, the representation of the treatment zone marker in the volumetric view is a wireframe.

In yet another aspect of the present disclosure, the 3D volume is centered on one of the target, a target marker, the treatment zone marker, or a distal portion of an instrument.

In an aspect of the present disclosure, the 3D volume is rotatable in response to a received user input.

In a further aspect of the present disclosure, the 3D volume has a shape selected from the group consisting of, a cubic shape, a rectangular shape, a pyramid shape, and a spherical shape.

In another aspect of the present disclosure, the at least one slice of the treatment zone setting view includes a representation of an instrument. In a further aspect of the present disclosure, an orientation and a position of the representation of the instrument is adjustable in response to a received user input to adjust an orientation and position of the treatment zone marker in the treatment zone setting view.

In yet a further aspect of the present disclosure, the volumetric view presents a 3D representation of the instrument. In an aspect of the present disclosure, adjustment of the orientation and position of the representation of the instrument in response to the received user input in the treatment zone setting view also adjusts a corresponding orientation and position of the 3D representation of the instrument and the orientation and position of the 3D treatment zone marker in the volumetric view.

In another aspect of the present disclosure, the representation of the instrument in the at least one slice of the treatment zone setting view includes a depth marker slidably disposed thereon, the depth marker slidable to set a depth of insertion of the instrument in response to a received user input.

In an aspect of the present disclosure, a non-transitory computer-readable storage medium is disclosed that is encoded with a program that, when executed by a processor, causes the processor to perform the steps of presenting at least one slice of a 3D reconstruction generated from CT image data including a target, presenting a treatment zone marker defining a location and a size of a treatment zone on the presented at least one slice of the 3D reconstruction, presenting a 3D volume derived from the 3D reconstruction, and presenting a 3D representation of the treatment zone marker relative to structures depicted in the 3D volume.

In another aspect of the present disclosure, the 3D representation of the treatment zone marker is a wireframe.

In yet another aspect of the present disclosure, the 3D volume is centered on one of the target, a target marker, the treatment zone marker, or a distal portion of an instrument.

In an aspect of the present disclosure, the computer program further causes the processor to rotate the 3D volume in response to a received user input.

In a further aspect of the present disclosure, the 3D volume has a shape selected from the group consisting of, a cubic shape, a rectangular shape, a pyramid shape, and a spherical shape.

In another aspect of the present disclosure, the computer program causes the processor to present a representation of an instrument in the at least one slice of the 3D reconstruction, to adjust an orientation and a position of the representation of the instrument in response to a received user input, and to adjust an orientation and a position of the treatment zone marker in the at least one slice of the 3D reconstruction in response to adjustment of the orientation and position of the representation of the instrument.

In a further aspect of the present disclosure, the computer program causes the processor to present a 3D representation of the instrument relative to structures depicted in the 3D volume, and to adjust an orientation and a position of the 3D representation of the instrument and the 3D representation of the treatment zone marker in response to adjustment of the orientation and position of the representation of the instrument and the orientation and position of the treatment zone marker in the at least one slice of the 3D reconstruction.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, of which.

DETAILED DESCRIPTION

The present disclosure provides a system and method for surgical treatment planning. The system presents a clinician with a streamlined method of treatment planning from the initial patient selection through a process of target identification and selection, target sizing, treatment zone sizing, entry point and route selection, and treatment plan review. The system also presents a clinician with the capability to compare and contrast pre-operative and post-operative CT image data to assess the outcome of a surgical treatment procedure that has been performed.

Although the present disclosure will be described in terms of specific illustrative embodiments, it will be readily apparent to those skilled in this art that various modifications, rearrangements and substitutions may be made without departing from the spirit of the present disclosure. The scope of the present disclosure is defined by the claims appended hereto.

Figure 1:
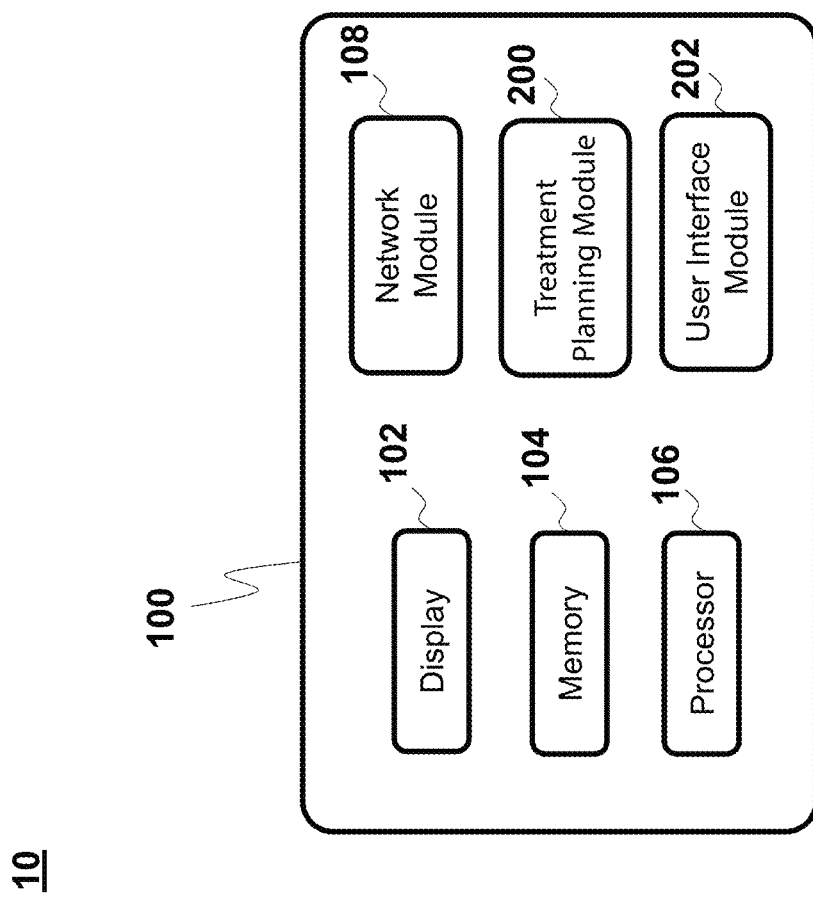
FIG. 1 is a schematic diagram of a computing device for treatment planning in accordance with an illustrative embodiment of the present disclosure.

Referring now to FIG. 1, the present disclosure is generally directed to a treatment planning system 10, which includes a computing device 100 such as, for example, a laptop, desktop, tablet, or other similar device, having a display 102, memory 104, one or more processors 106 and/or other components of the type typically found in a computing device. Display 102 may be touch sensitive and/or voice activated, enabling display 102 to serve as both an input and output device. Alternatively, a keyboard (not shown), mouse (not shown), or other data input devices may be employed.

Memory 104 includes any non-transitory, computer-readable storage media for storing data and/or software that is executable by processor 106 and which controls the operation of the computing device 100. In an embodiment, the memory 104 may include one or more solid-state storage devices such as flash memory chips. Alternatively or in addition to the one or more solid-state storage devices, memory 104 may include one or more mass storage devices connected to the processor 106 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 106. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 100.

Computing device 100 may also include a network module 108 connected to a distributed network or the internet via a wired or wireless connection for the transmission and reception of data to and from other sources. For example, computing device 100 may receive computed tomographic (CT) image data of a patient from a server, for example, a hospital server, internet server, or other similar servers, for use during surgical ablation planning. Patient CT image data may also be provided to computing device 100 via a removable memory 104.

A treatment planning module 200 includes a software program stored in memory 104 and executed by processor 106 of the computing device 100. As will be described in more detail below, treatment planning module 200 guides a clinician through a series of steps to identify a target, size the target, size a treatment zone, and determine an access route to the target for later use during a surgical procedure. Some examples of surgical procedures for which surgical treatment planning may be performed include ablation procedures, biopsy procedures, video-assisted thoracic surgery (VATS), open chest surgery, laparoscopic surgery, or any other type of surgery that could benefit from visualization and planning of the surgical procedure. Treatment planning module 200 communicates with a user interface module 202 which generates a user interface for presenting visual interactive features to a clinician, for example, on the display 102 and for receiving clinician input, for example, via a user input device. For example, user interface module 202 may generate a graphical user interface (GUI) and output the GUI to the display 102 for viewing by a clinician.

As used herein, the term "clinician" refers to any medical professional (i.e., doctor, surgeon, nurse, or the like) or other user of the treatment planning system 10 involved in planning, performing, monitoring and/or supervising a medical procedure involving the use of the embodiments described herein.

As used herein, the term "view" refers to any screen, image, overlay, user interface, window, or combination thereof, which may be projected on or output to the display 102 by user interface module 202.

Figure 2:
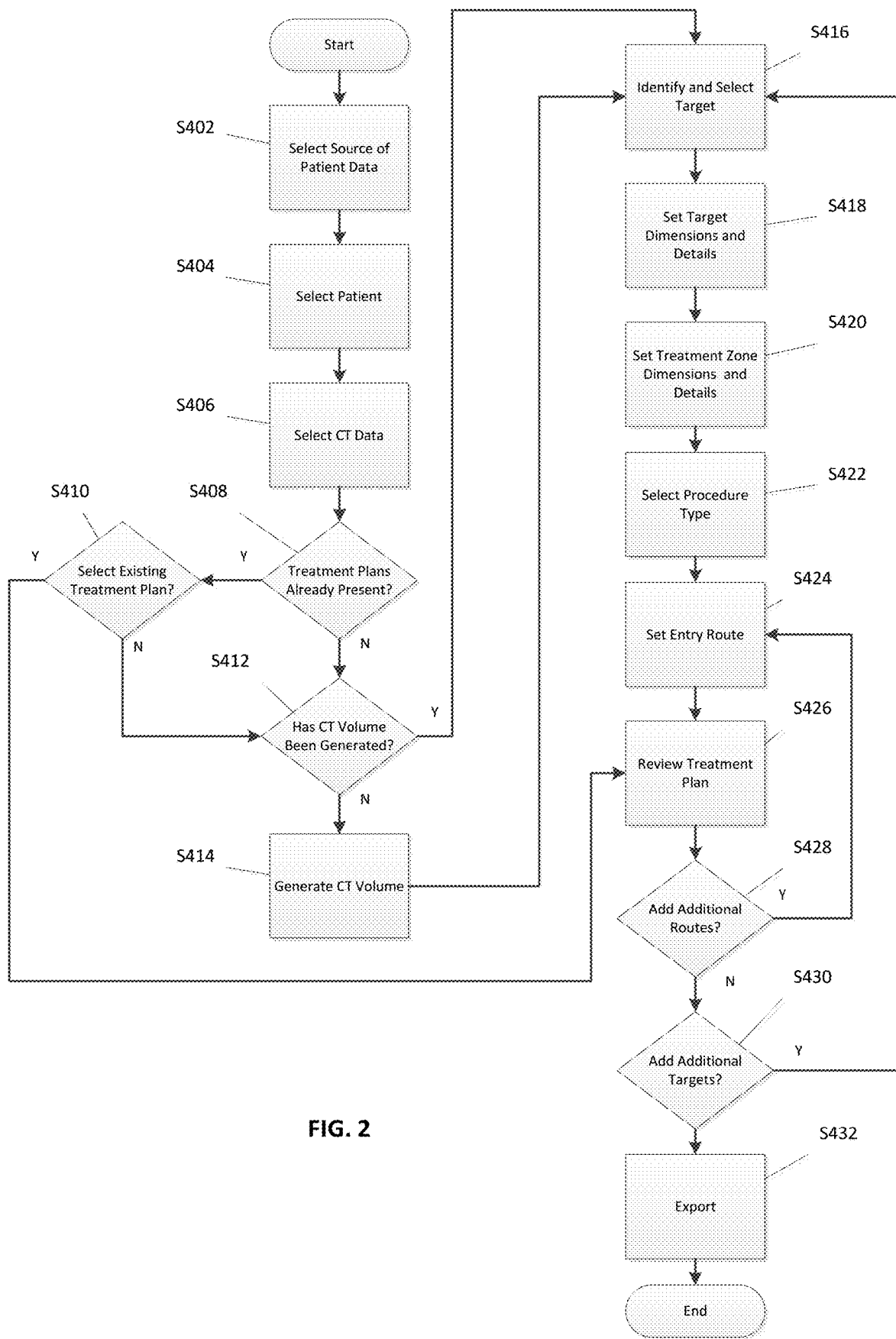
FIG. 2 is a flow chart illustrating a method of treatment planning in accordance with an embodiment of the present disclosure.
Figure 3A:
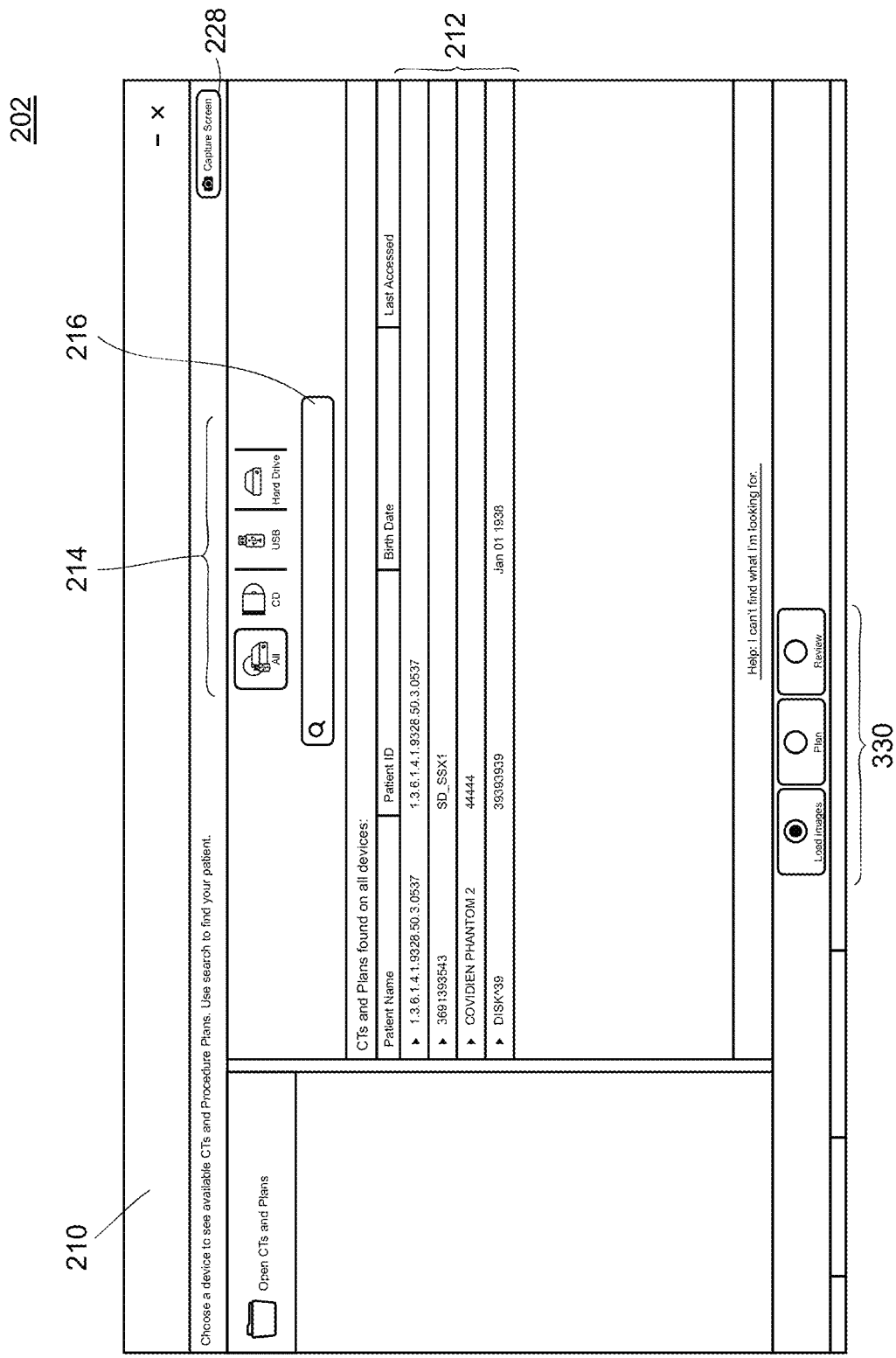
FIG. 3A is an illustration of a user interface presenting a view for the selection of patient data in accordance with an embodiment of the present disclosure.

FIG. 2 depicts an exemplary method of treatment planning using the treatment planning module 200 and the user interface module 202. Upon starting treatment planning module 200, the user interface module 202 presents the clinician with a view 210. As shown in FIG. 3A, view 210 includes a list of patient data sets 212 that are available for treatment planning. Each patient data set includes a patient identifier, for example, the patient's name or a unique patient ID, a date of birth, and patient CT image data for use during treatment planning. View 210 also includes a selectable source location menu 214 that allows the clinician to select a source from which patient data sets 212 are received for use in treatment planning. In step S402 the clinician selects from a number of storage or memory devices including, for example, CD, DVD, Blue-ray, other optical media, universal serial bus (USB) memory devices, external or internal hard drives, solid state storage devices, or any other type of memory or storage 104 connected to or in data communication with computing device 100, as described above. The view 210 may also provide access to patient data sets 212 stored in a remote location such as, for example, a server on a network or the internet. Source location menu 214 may allow the clinician to select a single source of patient data or may allow the clinician to select multiple sources of patient data at the same time. Source location menu 214 may also include an option to list patient data sets 212 from all sources, as shown in FIG. 3A. Having selected a data source, in step S404 the clinician selects the desired patient data set 212 corresponding to a patient requiring a new treatment plan or a patient whose treatment plan the clinician desires to review. The clinician may search through the list of patients data sets 212 or may input a search term in a search box 216 to narrow down the list of patients data sets 212 to those meeting a selected criteria such as, for example, a patient's first or last name, ID number, date of birth, last accessed, or other similar criteria.

Figure 3B:
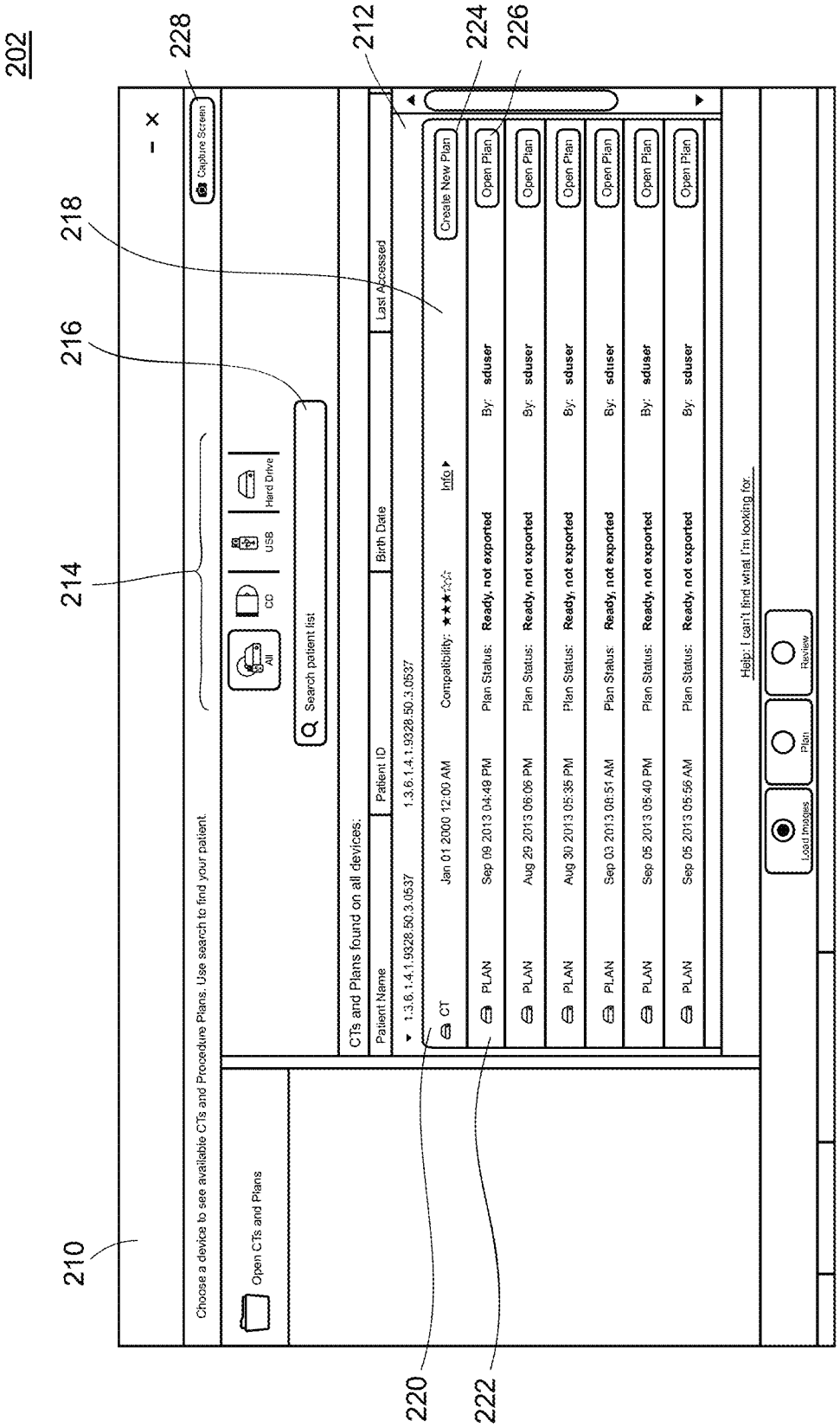
FIG. 3B is an illustration of the user interface of FIG. 3A presenting CT image data for a selected patient.

As shown in FIG. 3B, following selection of a patient data set 212, the user interface element expands to present a menu 218 to the clinician which includes a list of available CT image data 220 for the selected patient data set 212. Each available CT image data 220 is rated on a compatibility scale, for example, from one to five stars, to provide the clinician with an indication of whether a particular CT image data 220 is compatible with the treatment planning system 10. Indicators of compatibility of CT image data may include, for example, the thickness parameter of the CT scan, the interval parameter of the CT scan, image gaps, resolution of the CT scan, field of view (FOV), the number of images, or other similar parameters of the CT scan. Additionally, the date the CT image data 220 was captured and the date a treatment plan 222 was generated from the CT image data may also be displayed.

In step S406, the clinician selects a desired CT image data 220 from the list and in step S408 the treatment planning module 200 determines whether there are any treatment plans 222 already present for the selected CT image data 220. If a previously created treatment plan 222 is present for the selected CT image data 220, user interface module 202 presents the clinician with a list of available treatment plans 222 for review. In step S410, the clinician chooses to review a previously generated treatment plan 222 by selecting an open plan option 226 or to create a new treatment plan by selecting a create new plan option 224 from the menu.

View 210 also includes a capture screen option 228 that is selectable by the clinician to capture an image of the current screen shown on the display 102, for example, view 210, and save the captured image to memory. The capture screen option 228 may also be configured to remove patient specific data from the captured image to protect patient privacy. The removal of patient specific data may be an option selectable by the clinician and may be set to "on" by default. Any of the views described herein may include a capture screen option 228 as described above.

In step S412, when there are no treatment plans 222 already present or when the clinician has selected the create new plan option 224, the treatment planning module 200 determines if a 3D reconstruction of the 2D CT images (3D reconstruction) has been generated from selected CT image data 220. If a 3D reconstruction has not been previously generated, the CT image data 220 is imported into the treatment planning module 200 for processing in step S414, preferably in a DICOM format. In general, the computing device 100 processes the CT image data 220 and assembles the CT image data 220 into a 3D reconstruction by arranging the CT images in the order that they were taken and spacing the CT images apart according a distance between slices set on the CT scanning device when the CT image data 220 of the patient was taken by the CT scanning device. Treatment planning module 200 may also perform a data fill function to create a seamless 3D reconstruction from the CT image data 220. A variety of data manipulation and augmentation techniques which assist in rendering useable 2D and 3D structures that can be presented to and manipulated by the clinician in accordance with embodiments of the present disclosure are described in greater detail below. These data manipulation and augmentation techniques are well known to those of ordinary skill in the art and their use either individually or in combination can be undertaken without departing from the scope of the present disclosure.

Figure 4A:
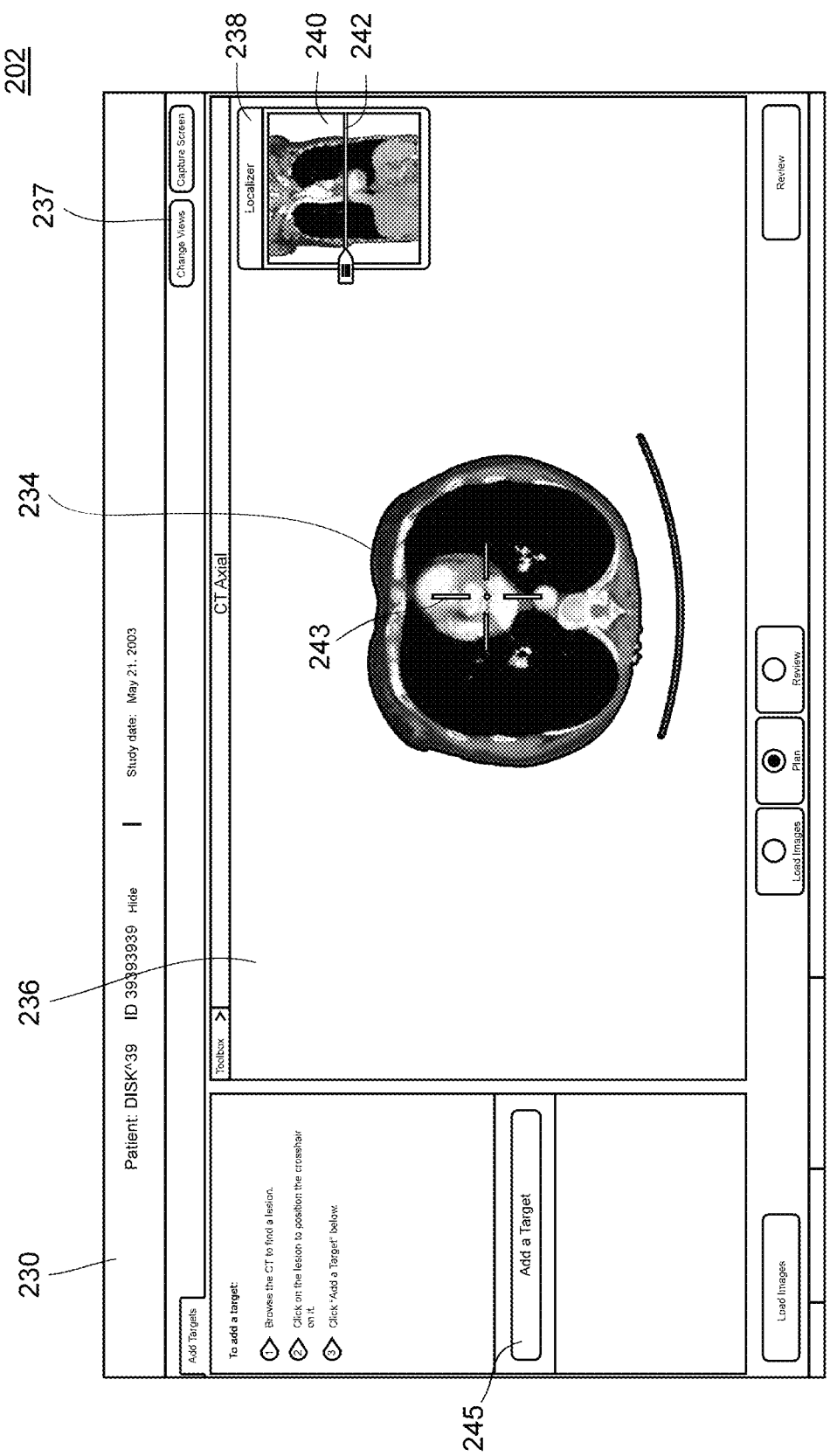
FIG. 4A is an illustration of a user interface presenting a view including an axial view CT slice for selecting and adding a target in accordance with an embodiment of the present disclosure.

With reference to FIG. 4A, once a 3D reconstruction has been generated for the selected CT data 220 or if the 3D reconstruction had been previously generated, user interface module 202 presents the clinician with a view 230 for identification and selection of a target in step S416. The view 230 may include identification data including the source of the CT image data 220 the patient ID, and the date of the treatment plan 222, as shown in the banner at the top of view 230. In view 230, the clinician is presented with a slice 234 of the generated 3D reconstruction in a main view 236. The slice 234 may be taken from the generated 3D reconstruction in any one of the axial, coronal and sagittal directions. The slice 234 may be a reformatted CT image, a maximum-intensity projection (MIP), minimum-intensity projection (mIP/MinIP) or other similar forms of presenting a slice 234 of the 3D reconstruction. FIG. 4A depicts the slice 234 of the 3D reconstruction viewed from the axial direction.

Figure 4B:
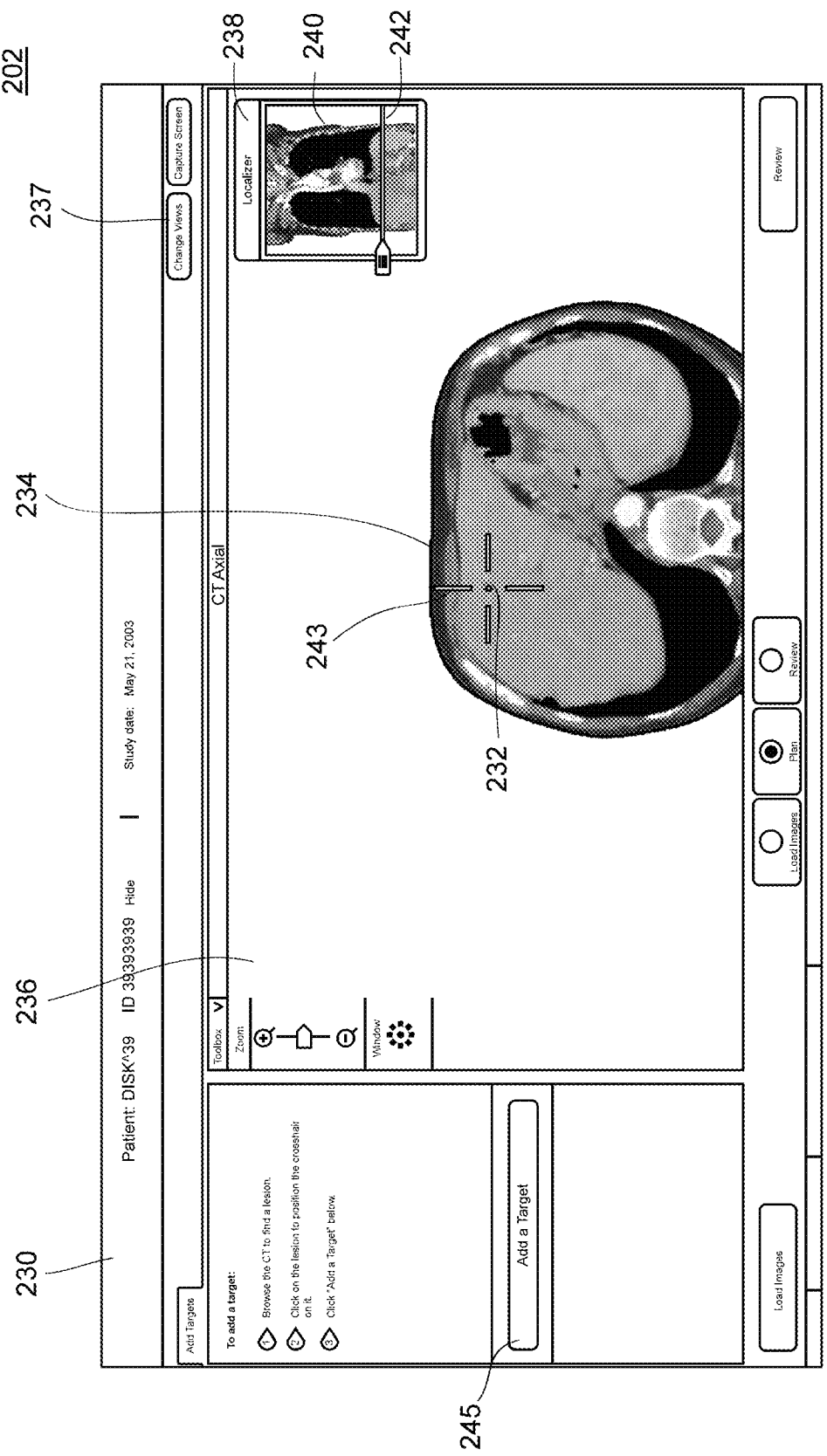
FIG. 4B is an illustration of the user interface of FIG. 4A illustrating an area of interest including a target in the axial view CT.
Figure 4C:
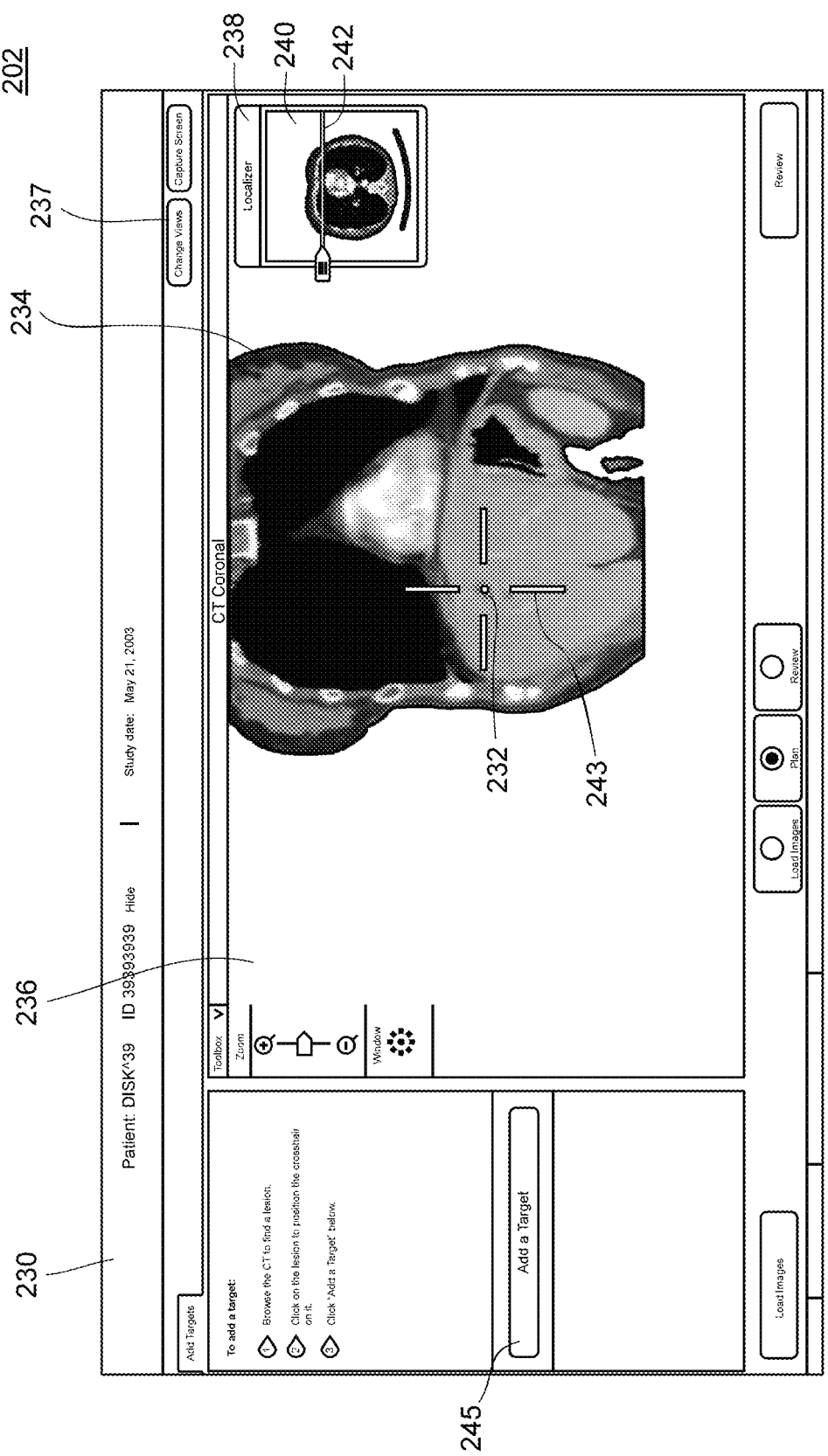
FIG. 4C is an illustration of the user interface of FIG. 4B presenting a coronal view CT slice including an illustration of the area of interest.

As shown in FIGS. 4B and 4C, the clinician may freely switch the slice 234 shown in the main view 236 between the axial, coronal, and sagittal directions at any time by activating a change views button 237. For example, FIG. 4B depicts main view 236 including an axial slice 234 of the 3D reconstruction while FIG. 4C, depicts main view 236 including a coronal slice 234 of the 3D reconstruction at the same location after the change views button 237 has been activated. In addition, the clinician may also activate the change views button 237 to switch between a reformatted slice and a MIP slice, to present a 3D rendered image of the patient, or to present the slice 234 in any other image format. Change views button 237 may alternatively be presented as a button bar 239 (FIGS. 6C and 10) separately presenting each of the slice or view options for easy activation by a clinician. The clinician may manipulate and relocate the image of the selected slice 234 in the main view 236 and may zoom in or out on the selected slice 234 to obtain an enlarged or reduced view of a particular portion of the selected slice 234. Generally it is useful for the clinician to only show a single slice and direction at a time, for example, only an axial slice 234 from the 3D reconstruction, thus the clinician is provided with a simple and clean interface from which to identify and select a target. The change views button 237, however, may also be activated to present a multi-plane view in the main view 236 including each of the axial, coronal, and sagittal slices at the same time should the clinician wish to see slices of all three directions at the same time. The multi-plane view may present a volumetric view 267 including a 3D volume 271 derived from the 3D reconstruction in addition to the axial, coronal, and sagittal slices, as described in more detail below with reference to FIG. 6C.

View 230 also includes a localizer 238 which provides a general overview of the 3D reconstruction for use by the clinician. As illustrated in FIGS. 4A and 4B, localizer 238 includes a localizer view 240 presenting a generic view of a patient's body, for example, the patient's chest, abdomen, and/or lungs, from the coronal direction. The localizer view 240 may, for example, present a reformatted CT image, a fluoroscopy-like image, a MIP image, MinIP image, or other similar images that present a clinician with a view of the region of interest in the patient's body. Localizer 238 includes a location element 242, for example, a line or bar, extending across localizer view 240 which provides a clinician with a location of the selected slice 234 presented in main view 236 relative to the patient's body as presented by the localizer 238.

Location element 242 is selectable by the clinician and moveable or slidable relative to the localizer view 240 to allow the clinician to scroll through the slices 234 of the 3D reconstruction of the patient's body presented on the main view 236. For example, the slices 234 may be scrolled through or presented in a sequential order defined by the 3D reconstruction as illustrated in FIGS. 4A and 4B. The clinician may also or alternatively click on or select a portion of the localizer view 240 to move the main view 236 to the selected slice of the 3D reconstruction. The clinician may also or alternatively scroll through the slices 234 of the 3D reconstruction of the patient's body presented in the main view 236 via an input device such as, for example, a mouse wheel or other device without interacting directly with main view 236 or localizer view 240. When the change views button 237 is activated and another direction is selected for present on main view 236, for example, the coronal direction, localizer 238 may present a generic view of one of the other directions, for example, the axial direction or the sagittal direction, as shown, for example, in FIG. 4C. Localizer 238 provides the clinician with a general reference for where a particular lesion or other target 232 is located in the patient's body. Localizer 238 may also present one or more previously selected targets for the clinician's reference.

As illustrated in FIG. 4B, when identifying a target in step S416, the clinician may scroll through the slices 234 in the main view 236 in the manner described above until the clinician identifies a slice 234 containing an area of interest. The clinician may also or alternatively determine potential areas of interest by looking at the localizer view 240 and may move the location element 242 to the potential area of interest to present the slice 234 containing the potential area of interest on the main view 236. For example, as shown in FIGS. 4B and 4C, a the clinician may identify a dark spot on the liver as the potential area of interest which may indicate a potential target 232, for example, a tumor, lesion, or the like.

Referring again to FIG. 4C, once a target 232 has been identified in the slice 234 shown in the main view 236, the clinician positions a target selection element 243 over the target 232 to select the target 232 for treatment planning. For example, the clinician may click on the target 232 using a user input device such as a mouse, keyboard, or other similar device to position the target selection element 243 over the target 232. The clinician may also or alternatively drag, slide, or manipulate the slice 234 presented on the main view 236 using the user input device until a stationary target selection element 243, for example, a target selection element 243 permanently centered in the main view 236, is positioned over the target 232. If display 102 is touch-sensitive, the clinician may also or alternatively touch the target 232 on display 102 to position the target selection element 243 over the target 232. Examples of target selection elements 243 include a crosshair, a mouse pointer, a hand selection tool, or other similar selection elements. In the multi-plane view a volumetric view 267 including a 3D volume 271 derived from the 3D reconstruction may be presented, as described in more detail below with reference to FIG. 6C. Once the target selection element 243 has been positioned over the target 232, the clinician may activate an add a target button 245 to select the target 232 for treatment planning.

Figure 5A:
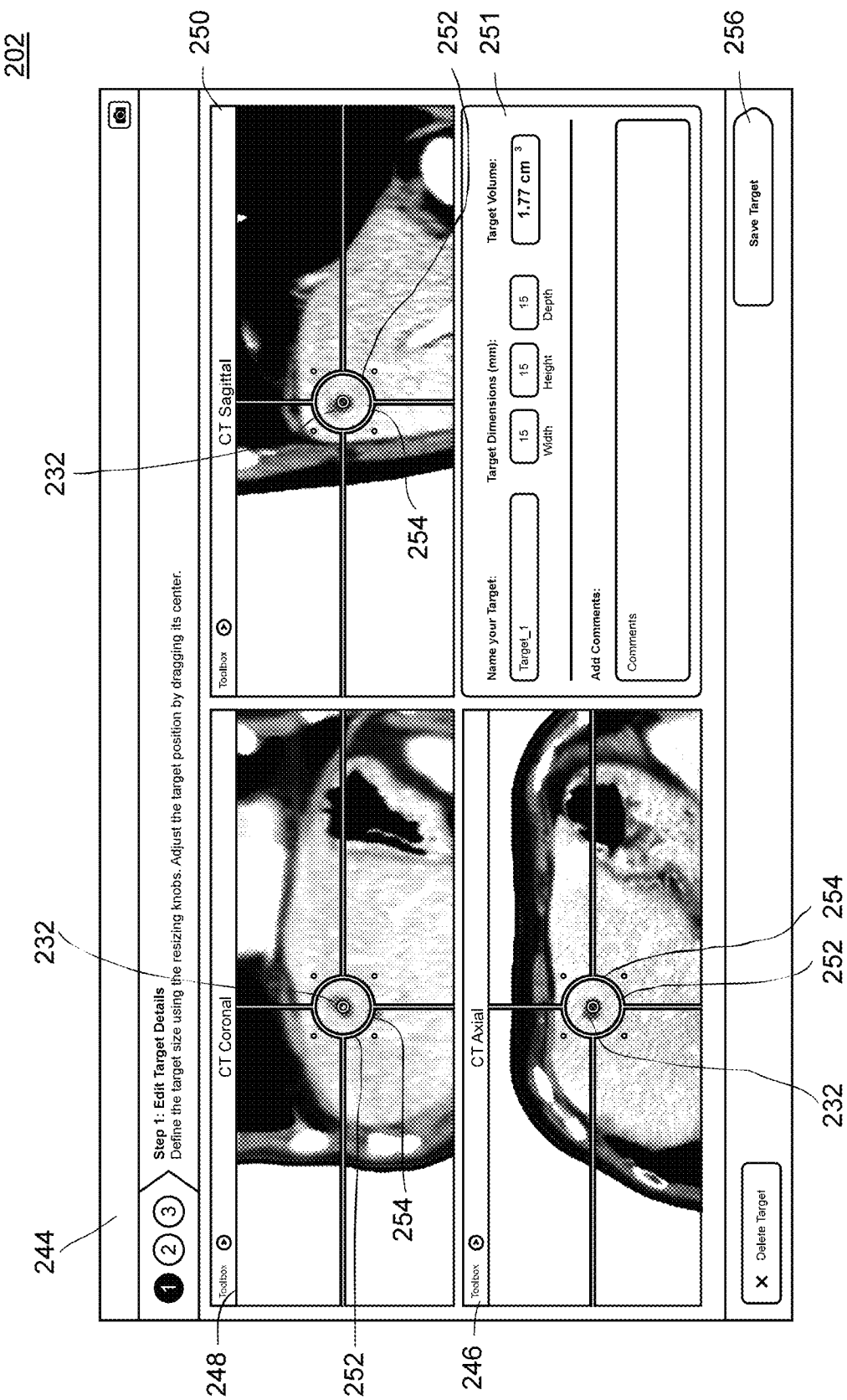
FIG. 5A is an illustration of a user interface presenting a view for editing target details of an added target in accordance with an embodiment of the present disclosure.

Once a target 232 has been selected for treatment planning by the clinician, user interface module 202 presents a target details view 244 to the clinician to allow the clinician to set the target dimensions and details in step S418, as shown in FIG. 5A. Target details view 244 may overlay view 230 or may replace view 230. Target details view 244 provides the clinician with the selected target 232 as shown in an axial slice 246 of the 3D reconstruction, a coronal slice 248 of the 3D reconstruction, a sagittal slice 250 of the 3D reconstruction, and a target details pane 251. The axial, coronal, and sagittal slices 246, 248, and 250 may be enlarged or zoomed in on the target 232 to provide the clinician with improved visibility of the target 232 and the surrounding area of interest. Target details view 244 may also present a volumetric view 267 including a 3D volume 271 derived from the 3D reconstruction, for example, as described in more detail below with reference to FIG. 6C. The volumetric view 267 may replace the target details pane 251. The clinician may also change views by activating a change views button (not shown) of target details view 244 in a similar manner to activating change views button 237 of view 230 as described above.

Figure 5B:
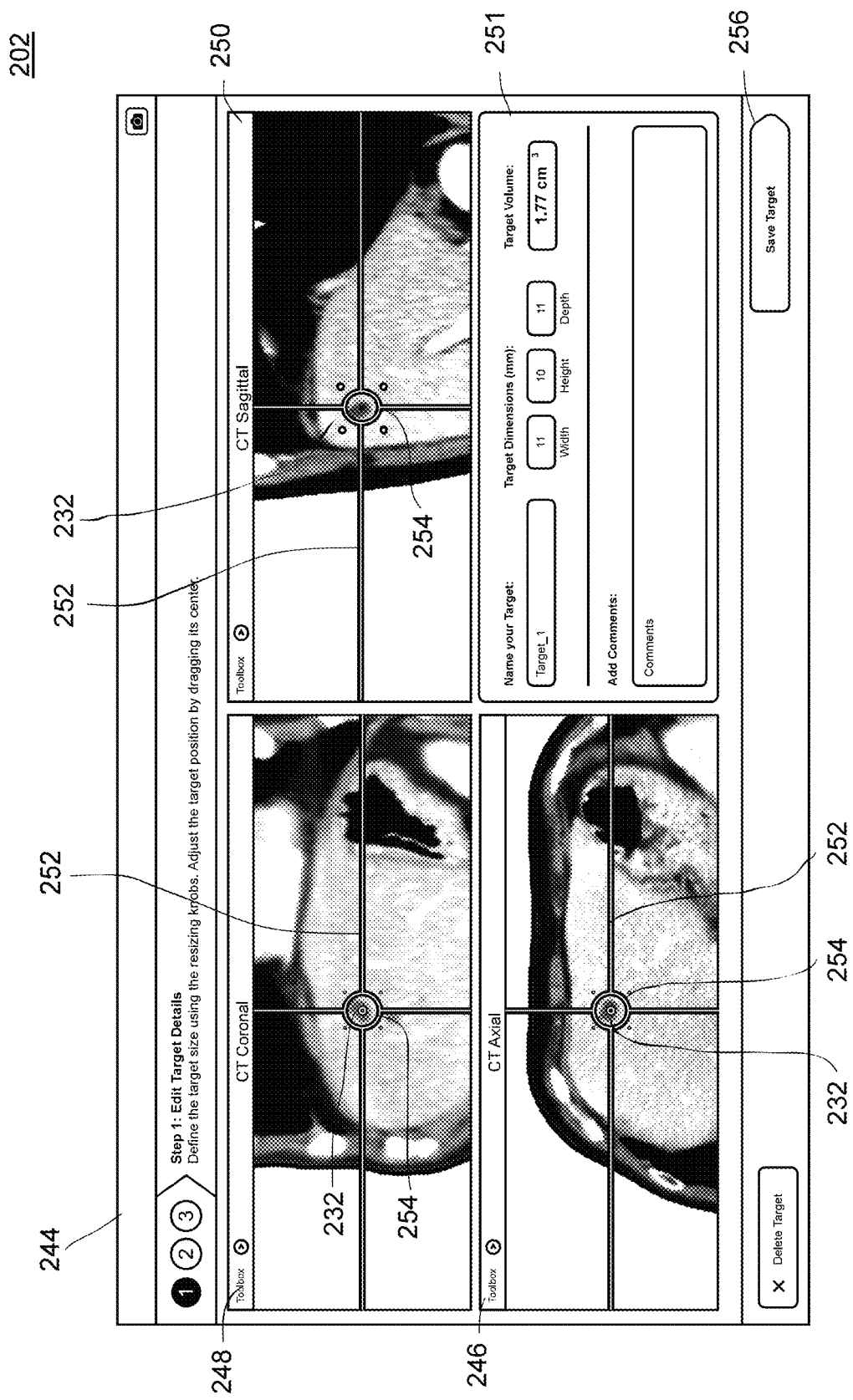
FIG. 5B is an illustration of the user interface of FIG. 5A illustrating a target marker sized to the added target.

When setting the target dimensions and details in step S418, the clinician may adjust the width, height, and depth dimensions for the target 232, name the target 232, and add additional comments relating to the target 232 in the target details view 251. In addition, a target marker 252, e.g., a crosshair or other similar element, is positioned over the target 232 in each of slices 246, 248, 250 and is manipulatable or movable by the clinician to center the target marker 252 over the target 232 in each slice 246, 248, 250. Target marker 252 also includes an adjustable boundary ring 254 that is manipulatable by the clinician to resize the dimensions of the target 232. For example, as shown in the difference between FIGS. 5A and 5B, the clinician may resize the boundary ring 254 on each of the axial slice 246, coronal slice 248, and sagittal slice 250 to accurately define or approximate the dimensions of the target 232. Boundary ring 254 may be circular, oval, or other geometric shapes and the shape of the boundary ring 254 may be adjusted to substantially match or closely approximate the general dimensions of the target 232, as shown in FIG. 5B. In an embodiment, boundary ring 254 may be adjusted in a non-geometric manner by the clinician, for example, a free-form manipulation of boundary ring 254, to conform to non-geometric dimensions of the target 232. It is important to note that because the target 232 is a three dimensional object such as, for example, a lesion, tumor, or the like, and each of the axial, coronal, and sagittal slices 246, 248, 250 is taken from a different direction, manipulation and adjustment of the boundary ring 254 in one of the slices 246, 248, 250 by the clinician may result in a change or adjustment of the boundary ring 254 in one or both of the remaining slices 246, 248, 250. In this manner the clinician may accurately set the target dimensions and the location of the target 232 in all three views, effectively mapping the target to specific coordinates and dimensions in a 3D coordinate space. The clinician may also be presented with the option to set a surgical margin about the target 232 based on the target marker 252 when the clinician is planning a lung resection treatment procedure. For example, the surgical margin may have a default setting of about 2.5 times the diameter of the largest axis of the target marker 252 and may be adjustable by the clinician to increase or decrease the size of the surgical margin. Once the dimensions and location of target 232 have been set by the clinician, the clinician may activate the save target button 256 to save the target dimensions and details and proceeds to setting the treatment zone in step S420.

Figure 6A:
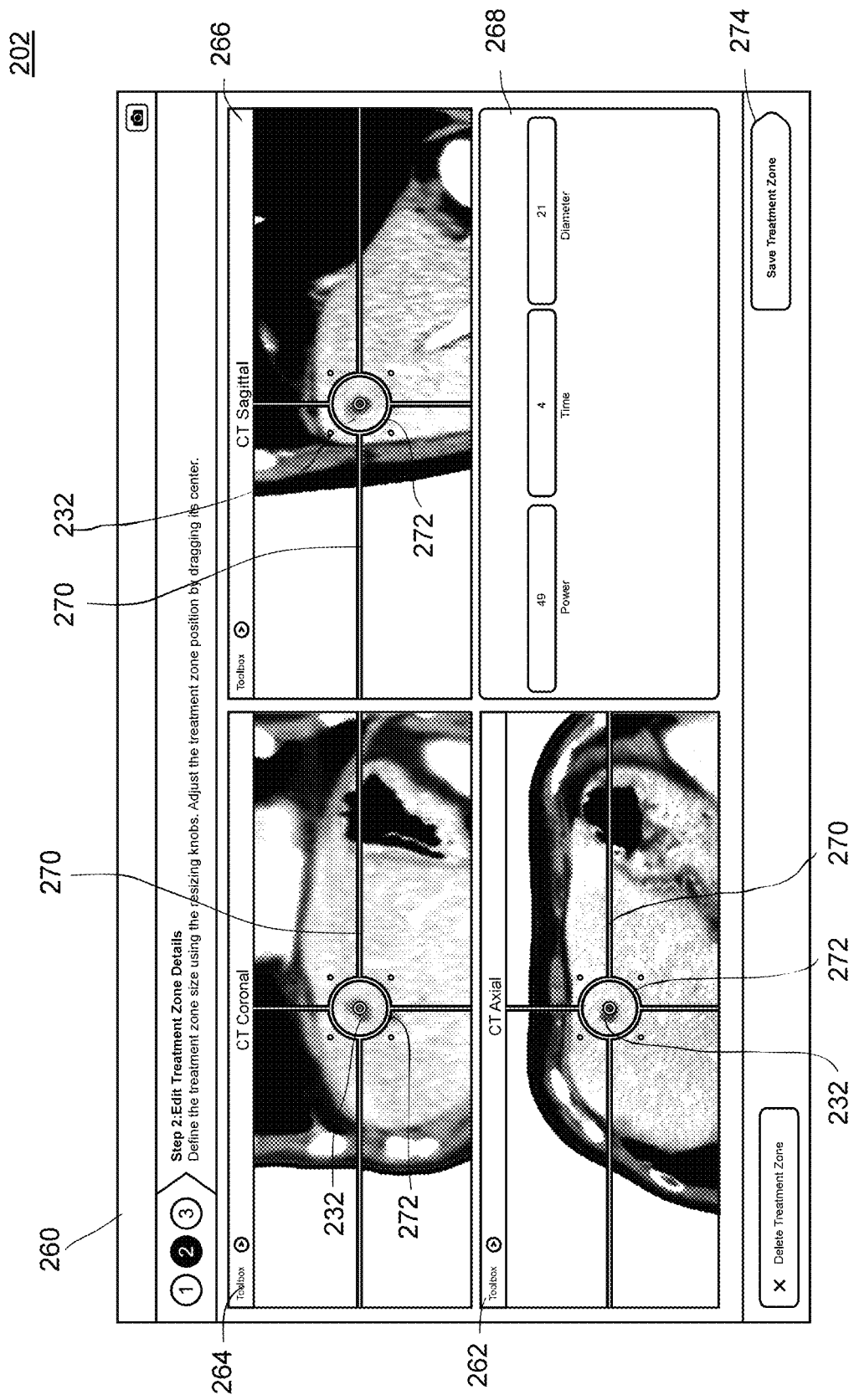
FIG. 6A is an illustration of a user interface presenting a view for editing treatment zone details in accordance with an embodiment of the present disclosure.

During setting of the treatment zone, user interface module 202 presents a treatment zone view 260 to the clinician, as shown in FIG. 6A. View 260 may overlay view 230 and replace view 244 or view 260 may replace both view 230 and view 244. Treatment zone view 260 provides the clinician with the selected target 232 as shown in an axial slice 262, coronal slice 264, and sagittal slice 266, and also provides a treatment zone details pane 268. The axial, coronal, and sagittal slices 262, 264, and 266 may be enlarged or zoomed in on the target 232 to provide the clinician with improved visibility of the target 232 and the surrounding area of interest. The clinician may also change views by activating a change views button (not shown) of target details view 244 in a similar manner to activating change views button 237 of view 230, as described above.

Figure 6B:
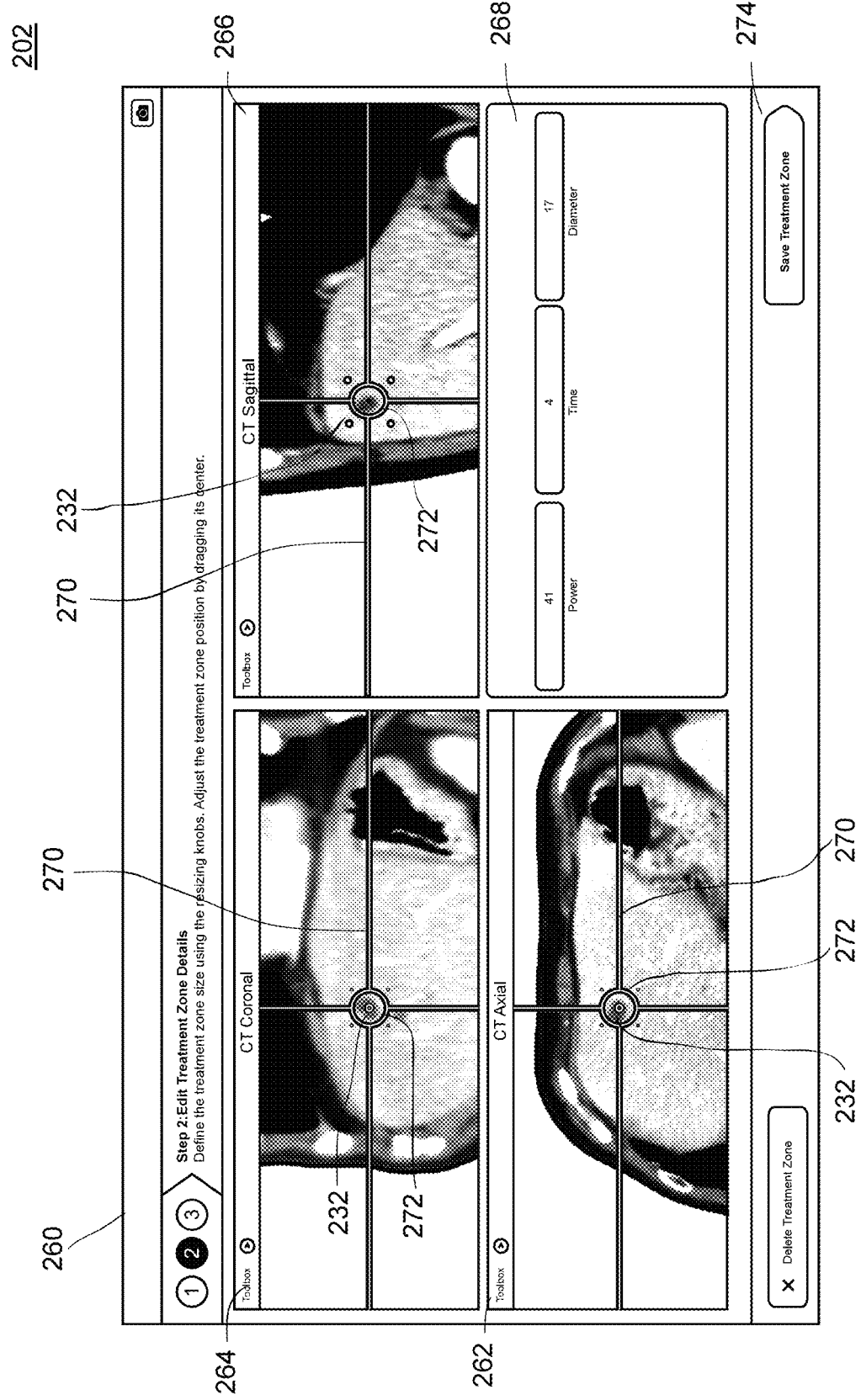
FIG. 6B is an illustration of the user interface of FIG. 6A illustrating a treatment zone marker sized relative to a target.
Figure 6C:
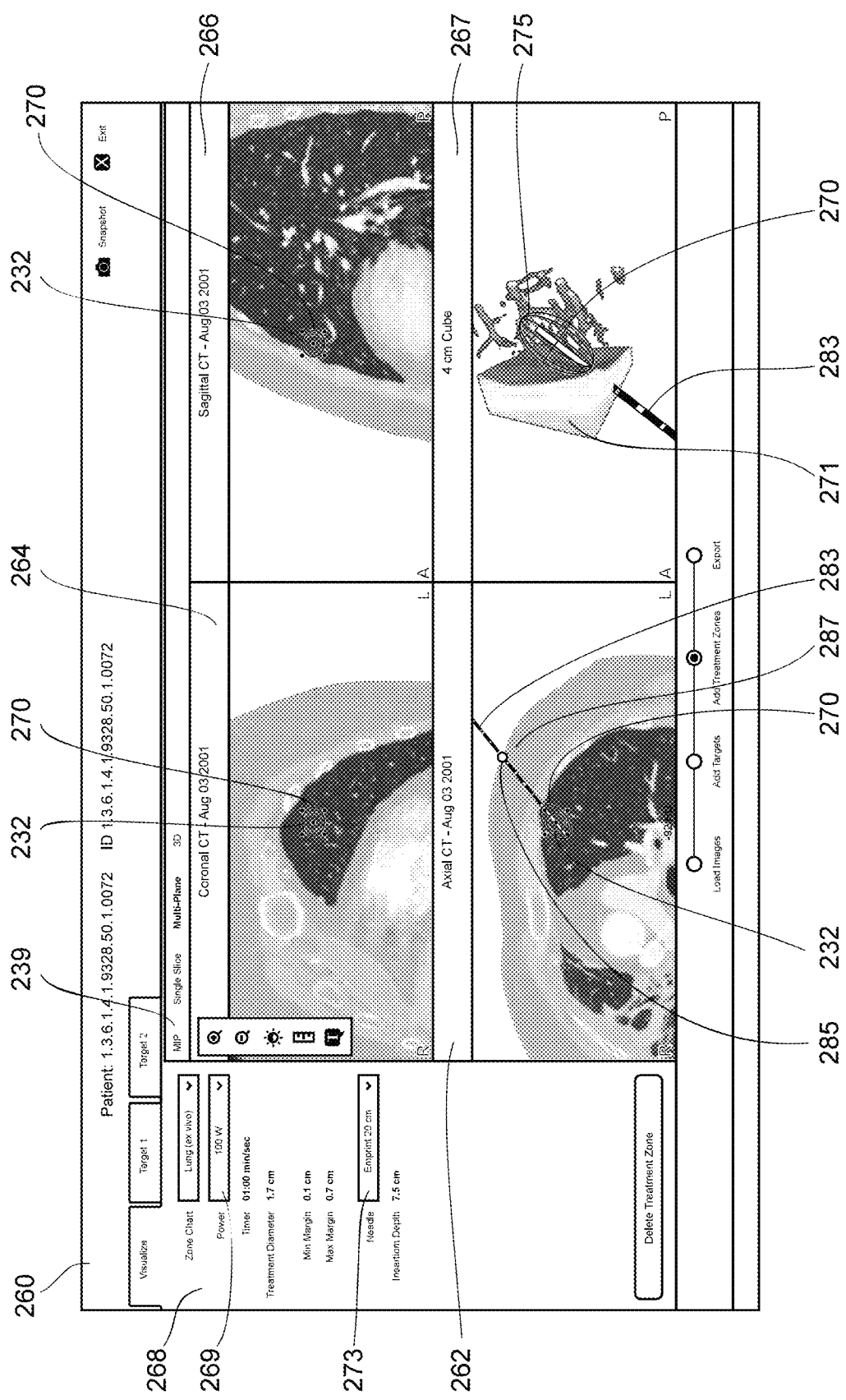
FIG. 6C is an illustration of a user interface presenting a view for editing treatment zone details in accordance with an embodiment of the present disclosure.

As shown in FIG. 6C, the treatment zone view 260 may also present a volumetric view 267 including a 3D volume 271 derived from the 3D reconstruction. The 3D volume 271 may be rendered through surface rendering, volume rendering, or the like and presents the clinician with a visual understanding of the target location and surrounding anatomical structures. For example, 3D volume 271 may be centered on one of the target 232, target marker 252, treatment zone marker 270, a distal portion of the representation of needle 283 or instrument 315 (FIG. 10), or any other feature that may require further visual inspection by a clinician. The 3D volume 271 may be a cubic shape, rectangular shape, pyramid shape, spherical shape or may have any other shape as required or desired by the clinician. As an example, the size of 3D volume 271 is preferably sufficiently large to encompass the selected target 232 and the treatment zone marker 270. For example, the size of 3D volume 271 may be from about 1 cm×1 cm×1 cm to about 10 cm×10 cm×10 cm and in an embodiment may be 4 cm×4 cm×4 cm. It is contemplated that the size of 3D volume 271 may be smaller than 1 cm×1 cm×1 cm or larger than 10 cm×10 cm×10 cm in any direction as needed. The presented 3D volume 271 may include, for example, airways, blood vessels, tissue boundaries, and/or any other relevant anatomical features for the clinicians review. The 3D volume 271 may also be rotatable by the clinician by clicking and dragging on the 3D volume 271 or utilizing other user inputs and may be enlarged or reduced in size through the use of tool box 332, as described below.

In the treatment zone details pane 268, the clinician may review and adjust the details and settings of the treatment zone. For example, the clinician may select, input, or adjust needle type (FIG. 6C), power level, duration (time), diameter, minimum margin, and/or maximum margin parameters for the treatment zone. The clinician may also or alternatively be presented with selectable preset power level settings 269 (FIGS. 6C and 10) including, for example, 45 W, 50 W, 75 W, and 100 W power levels settings. Other preset power level settings 269 are also contemplated. The preset power level settings 269 may also correspond to a particular needle type available for treatment in a surgical ablation procedure. As shown in FIG. 6C, the clinician may also or alternatively be presented with a selectable needle setting 273 that allows the clinician to select between different types of needles, different needle lengths, or various other needle related settings.

Still referring to FIG. 6A, a treatment zone marker 270, e.g., a crosshair or other similar element, is positioned over the target 232 in each of slices 262, 264, 266 and is movable by the clinician adjust the location of the treatment zone relative to the target 232. Treatment zone marker 270 also includes an adjustable boundary ring 272 in each slice 262, 264, 266 that is adjustable by the clinician to resize the treatment zone relative to the target 232. For example, the clinician may resize the boundary ring 272 on each of the axial slice 262, coronal slice 264 and sagittal slice 266 by adjusting at least one dimension of the boundary ring 272 to accurately define the treatment zone relative to the target 232. Boundary ring 272 may be, for example, a circle, oval or other similar geometric shapes and the shape of the boundary ring 272 may be adjusted to define a treatment zone that is preferably equal to or larger than the dimensions of the target 232. Alternatively, the clinician may adjust the boundary ring 272 to define a treatment zone that is smaller than the dimensions of the target 232. As shown in FIG. 6C, a 3D representation of the treatment zone marker 270 in may be presented in the volumetric view 267 to provide the clinician with an indication of the treatment zone in three dimensions. For example, the treatment zone marker 270 may be presented as a wireframe 275 in the volumetric view 267. Alternatively, the treatment zone 270 may be presented in the volumetric view 267 using surface rendering, volume rendering, or other similar techniques. Adjustment of the orientation and/or position of the treatment zone marker 270 in any of the axial slice 262, coronal slice 264, or sagittal slice 266, may also automatically adjust the orientation and/or position of the 3D representation of the treatment zone marker 270 presented in the volumetric view 267.

During a typical surgical treatment planning procedure, the treatment zone is sized by default to be slightly larger than the target 232 so that the clinician can ensure that the target 232 is completely treated. For example, the treatment zone may be set by default to a 5 mm margin for a target 232 in the lungs and may be set to a 1 cm margin for a target 232 in the liver. In one embodiment, because the target 232 is a three dimensional object such as, for example, a lesion, tumor, or the like, and each of the axial, coronal, and sagittal slices 262, 264, 266 is taken from a different direction, manipulation and adjustment of a dimension of the boundary ring 272 on one of the slices 262, 264, 266 by the clinician may result in a change or adjustment of a dimension of the boundary ring 272 in one or both of the remaining views 262, 264, 266.

When the treatment zone marker 270 is adjusted by the clinician, the treatment parameters, e.g., power, time, and diameter, may also be automatically adjusted. For example, as illustrated in the difference between FIGS. 6A and 6B, as the diameter of boundary ring 272 is reduced from 21 to 17, the required power is reduced from 49 to 41, and the time remains the same at 4. When a specific power level setting 269 (FIGS. 6C and 10) is preset or selected by a clinician, e.g., 50 W, 75 W, or 100 W, the user interface module 202 may present an indication or alert to the clinician when the clinician adjusts the diameter of the boundary ring 272 to a diameter that is larger than a predetermined maximum threshold or smaller than a predetermined minimum threshold. For example, each power level setting may include predetermined maximum and minimum diameter thresholds for the boundary ring 272. Alternatively, clinician may only be able to adjust the boundary ring 272 between the predetermined minimum and maximum thresholds and may be inhibited from adjusting the boundary ring beyond the predetermined minimum and maximum thresholds. Selection of a treatment needle with the selectable needle setting 273 (FIG. 6C) may also set the predetermined minimum and maximum thresholds based on the properties of the selected treatment needle.

The treatment zone marker 270 may also be adjusted or shaped to correspond to the treatment zone characteristics of a particular treatment probe or needle, for example, an oval shaped treatment zone or a circular shaped treatment zone. Alternatively, the choice of an appropriate treatment probe for the treatment procedure may be determined based on the size, shape, or other parameters of the treatment zone set by the clinician using the treatment zone marker 270 or the treatment zone details view 268. In this manner the clinician may accurately set the treatment zone dimensions relative to the target 232 in all three of the axial, coronal, and sagittal slices, effectively mapping the treatment zone to specific coordinates and dimensions in a 3-D coordinate space. Once the dimensions and location of the treatment zone have been set by the clinician the clinician may activate the save treatment zone button 274 and proceed to setting an entry route to the treatment zone in step S422.

In one embodiment, once the target dimensions and the treatment zone have been set, the clinician may be presented with the option to select between a number of different treatment procedures for accessing the target 232. For example, the clinician may be presented with a list of available treatment procedures from which to select an appropriate or desired treatment procedure. Alternatively, the clinician may be presented with the opportunity to select the type of procedure prior to any of the previous steps of the treatment planning method without departing from the scope of the present disclosure. For example, the clinician may select the type of treatment procedure before or after selecting the patient in step S402, after selecting CT data 202 in step S406, after selecting an existing treatment plan or creating a new treatment plan, after identifying and selecting a target in step S416, after setting the target dimensions and details in step S418, or after setting treatment zone dimensions and details in step S420. As an example, depending on when the type of treatment procedure is selected in the process, various features and/or settings of the procedure planning software may be adjusted to match the selected procedure type for each subsequent step.

The available treatment procedures may be based on the type of target 232, the location of target 232, the size of target 232, the size of the treatment zone, or any other factor or variable which may provide a clinician with an indication of a preferred treatment procedure. Examples of treatment procedures which may be selected or available to the clinician include open chest thoracic surgery, video assisted thoracic surgery (VATS), endoscopic surgery, cardiac ablation, cryoablation, focused ultrasound ablation, laser ablation, radiofrequency ablation, biopsy procedures, bronchoscopy, lung resection procedures, or any other type of procedure for treating a target 232. For example, the clinician may be presented with the option to select an intraluminal procedure and plan a pathway to the target as disclosed in co-pending application Ser. No. 13/838,805 entitled "Pathway Planning System and Method" the entirety of which is incorporated herein by reference.

Figure 7:
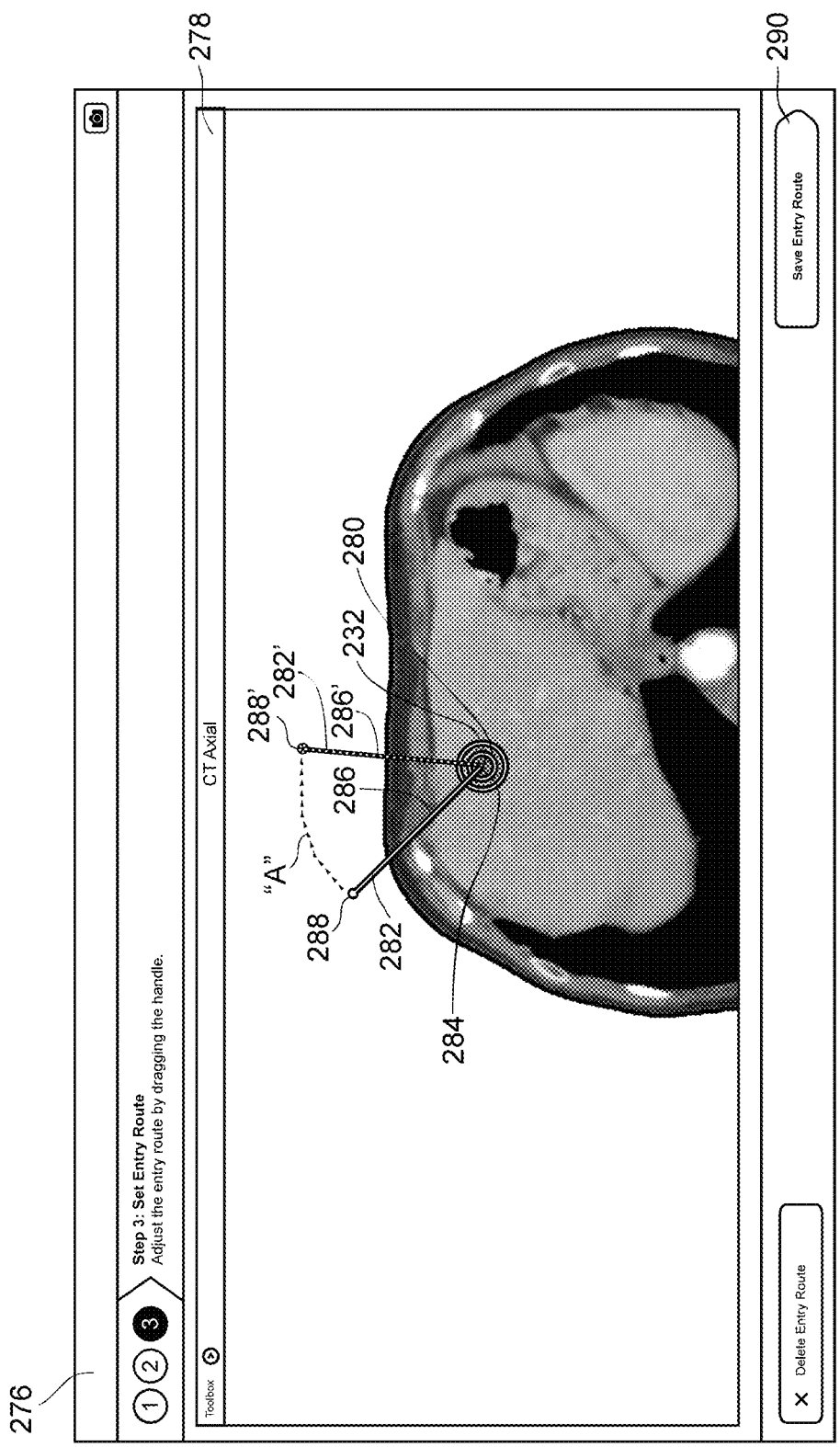
FIG. 7 is an illustration of a user interface presenting a view for setting an entry route to the target in accordance with an embodiment of the present disclosure.

Once the clinician has selected the desired procedure, in the example discussed in detail here, a percutaneous liver ablation procedure requiring access through the thoracic cavity, user interface module 202 presents a view 276 to the clinician for setting an entry route to the target 232 in step S424, as shown in FIG. 7. View 276 may overlay view 230 and replace view 260 or view 276 may replace both view 230 and view 260. View 276 provides the clinician with the selected target 232 presented in an axial slice 278. Other view CT slices could alternatively be presented if they provide a clear viewpoint for the clinician in assessing the entry route to the target 232, accordingly, view 276 may alternatively present the selected target 232 in a coronal slice or a sagittal slice. The clinician may also change views by activating a change views button (not shown) of view 276 in a similar manner to activating change views button 237 of view 230 as described above. Alternatively, the clinician may set the entry route in treatment zone view 260 in the manner described below for view 276 without user interface 202 presenting a new view 276.

View 276 includes a target marker 280 indicating a position of the target 232 and an entry route marker 282 extending from the target marker 280. The entry route marker 282 includes a first end 284 located at a center of the target marker 280, an entry route line 286 extending from the first end 284, and a second end 288. First end 284 is anchored to the target 232 and may be centered with respect to the target 232. Second end 288 is moved by the clinician to adjust the entry route line 286. For example, as shown in FIG. 7, the second end 288 may be moved by the clinician in a direction "A" to a location where second end 288' is outside the body such that the entry route line 286' of the moved entry route marker 282' does not contact ribs or other anatomical features which are undesirable for an entry route. In an embodiment, entry route line 286 is a linear line or trajectory illustrating a route or pathway for accessing the target 232 with a treatment instrument. Alternatively, entry route line 286 may be curved if the selected procedure includes the use of a flexible catheter or probe through an access portal. Once the position of the entry route marker 282' has been set, the clinician may save the entry route by activating the save entry route button 290. In an embodiment, as shown in FIG. 6C, the entry route line may be depicted as a representation of a probe or needle 283 inserted into the target 232. The needle 283 may be shown in any of the axial slice 262, coronal slice 264, and sagittal slice 266. The clinician manipulates the needle 283 in a similar manner as described above for entry route marker 282 to set the entry route to the target 232. In addition, a depth marker 285 positioned on the needle 283 is slidable by a clinician relative to the needle 283 to set a depth measurement of the needle 283 relative to a displayed tissue wall 287. The needle 283 may also be represented in the volumetric view 267 as extending into the 3D volume 271 to provide the clinician with an indication of the needle position relative to anatomical structures within the 3D volume 271 near the target 232. Manipulation or adjustment of the orientation and/or position of the needle 283 or treatment zone marker 270 in any of the axial slice 262, coronal slice 264, or sagittal slice 266, may also manipulate or adjust the orientation and/or position of 3D representation of the needle 283 or 3D representation of the treatment zone marker 270 presented in the volumetric view 267.

In other types of selected procedures, for example a VATS procedure, an additional route line 286 may be displayed to identify the location and placement of the laparoscopic imaging components. Similarly, where a Single Incision Laparoscopic Surgery (SILS) port is to be employed, the placement of the SILS port may be represented and manipulated by the clinician to improve its placement on the patient. In one embodiment where two or more surgical instruments are to be deployed the system may provide the clinician the option to add additional instruments as necessary for the contemplated surgery.

Figure 8:
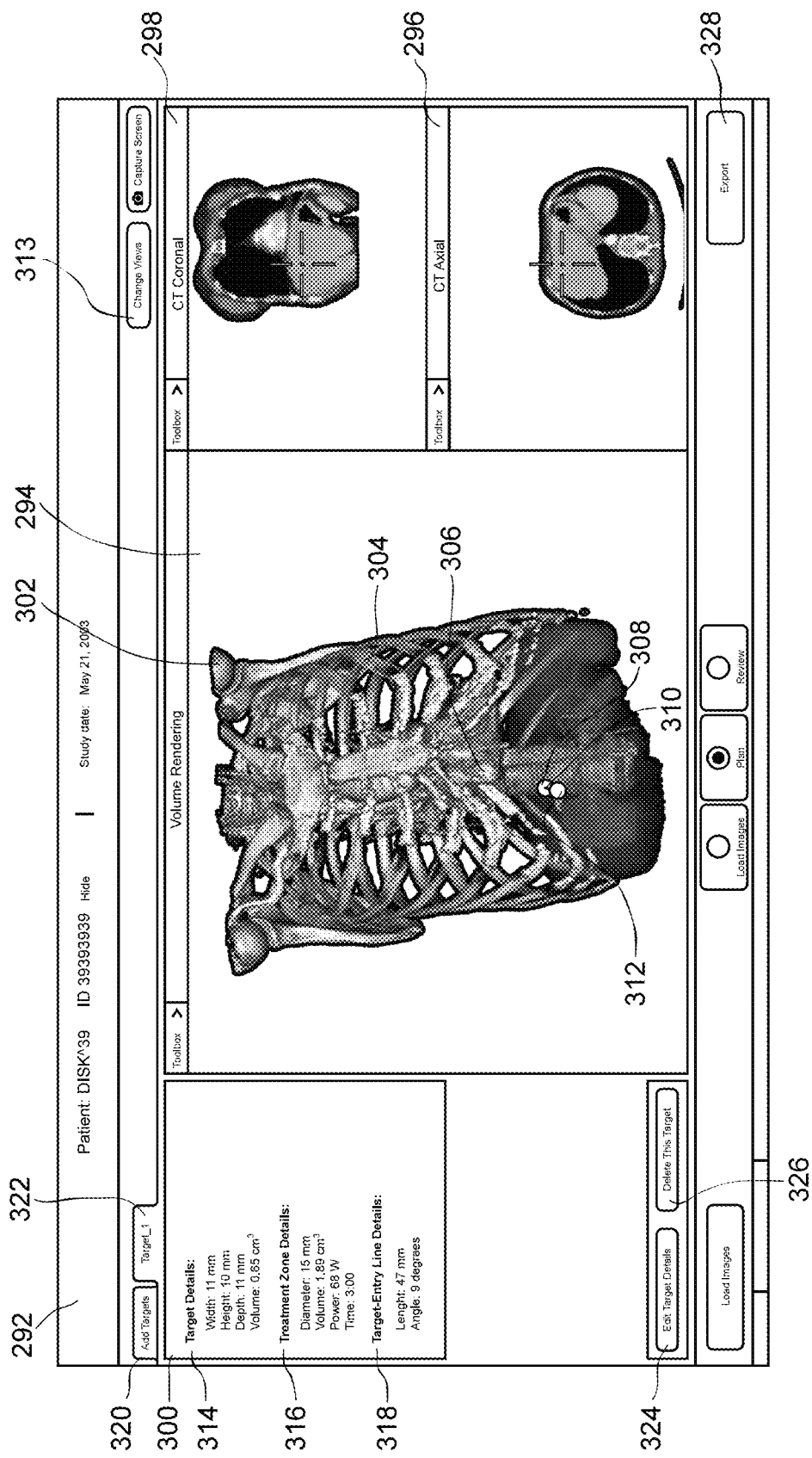
FIG. 8 is an illustration of a user interface presenting a view for reviewing a 3D model of the treatment plan in accordance with an embodiment of the present disclosure.

After the entry route has been set in step S424 or if the clinician selects an existing treatment plan in step S410, user interface module 202 presents the clinician with a view 292 for reviewing the treatment plan in step S426. As shown in FIG. 8, for example, view 292 includes main view 294, an axial slice 296, a coronal slice 298, and a details pane 300. Main view 294 includes a 3D model 302 of the patient's torso and abdomen generated by volume rendering, surface rendering, or a combination of volume rendering and surface rendering. Various rendering techniques that may be used to generate 3D model 302 will be described in more detail below. Alternatively, the clinician may review the treatment plan in treatment zone view 260 in the manner described below for view 294 without user interface 202 presenting a new view 294.

Figure 10:
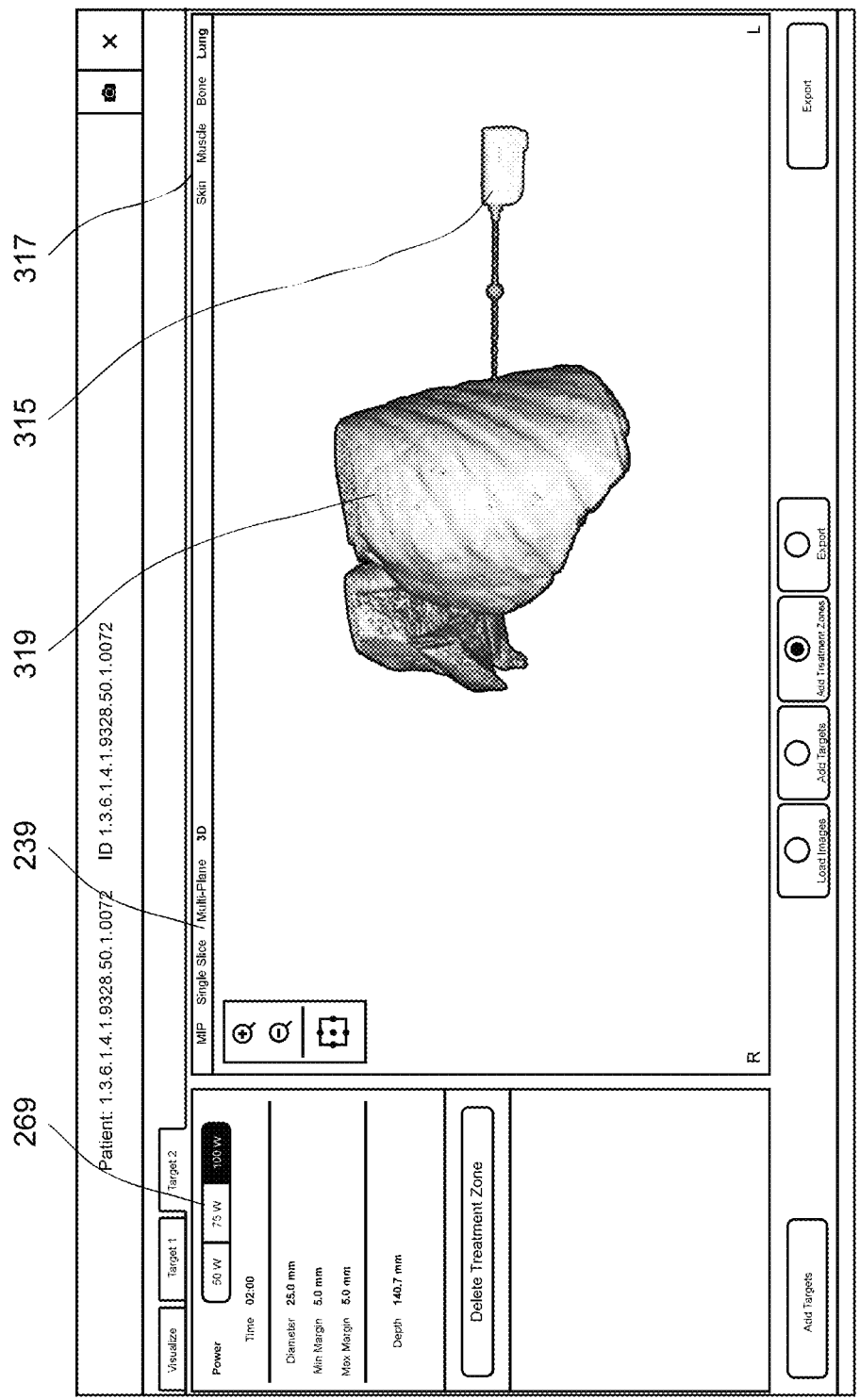
FIG. 10 is an illustration of a user interface presenting a view illustrating a representation of a patient's lung rendered in a 3D model and including a representation of an instrument positioned along an entry route in accordance with an embodiment of the present disclosure.

The 3D model 302 provides the clinician with a representation of the patient's anatomy and, in an exemplary embodiment, a representation of the patient's chest and thoracic cavity, as shown in FIG. 8. The 3D model 302 presents the clinician with multiple layers of the patient's anatomy including, for example, representations of the patient's skin, muscle, blood vessels, bones, airways, lungs, other internal organs, or other features of the patient's anatomy. For example, as shown in FIG. 8, main view 294 presents a 3D model 302 of the patient's thoracic cavity with the outer layers peeled back, removed, or adjusted to present a layer including the patient's ribs 304 and layers including other anatomical features 306 of the patient's internal anatomy to the clinician. The layers 304, 306 may be presented at different levels of opacity or transparency to allow the clinician to review the interior of the patient's torso relative to the treatment zone. The 3D model 302 may be rotated by activating a user input to allow the clinician to view the treatment plan from various angles and directions. The clinician may also activate a user input to peel back, remove, or adjust the opacity and translucence of each layer of the 3D model to provide the clinician with a visual representation of the planned entry route to the treatment zone relative to surrounding critical structures within the patient's body. For example, the clinician may activate the change views button 313 or a change view button bar 317 (FIG. 10), and select specific layers to be presented in model 302 or to adjust the opacity or translucence of each individual layer. For example, as shown in FIG. 10, a representation of a patient's lung 319 is presented upon selection of a lung layer from the change view button bar 317.

Still referring to FIG. 8, 3D model 302 includes a treatment zone marker 308 and an entry route marker 310. Treatment zone marker 308 is represented as a three-dimensional volume within the 3D model 302 and may be presented in a visually distinct or contrasting color as compared to the rest of the 3D model 302. As an example, the treatment zone marker 308 may be presented in a bright green color. The treatment zone marker 308 is sized to match the treatment zone set during step S420. Entry route marker 310 extends from treatment zone marker 308 out of the body to an end point 312 as set during step S424.

Figure 9:
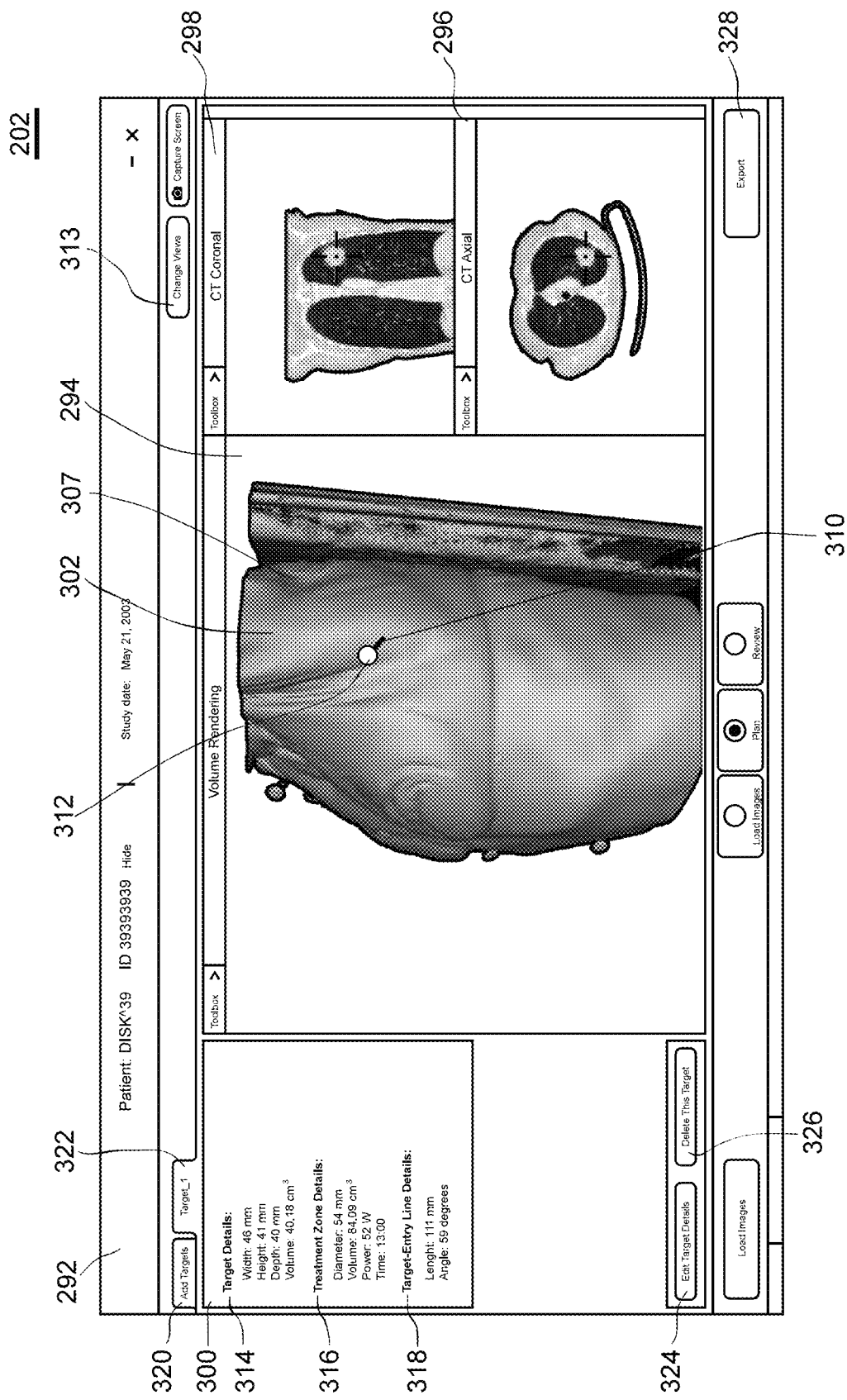
FIG. 9 is an illustration of the user interface of FIG. 8 illustrating a representation of a patient's skin rendered over the 3D model.
Figure 11:
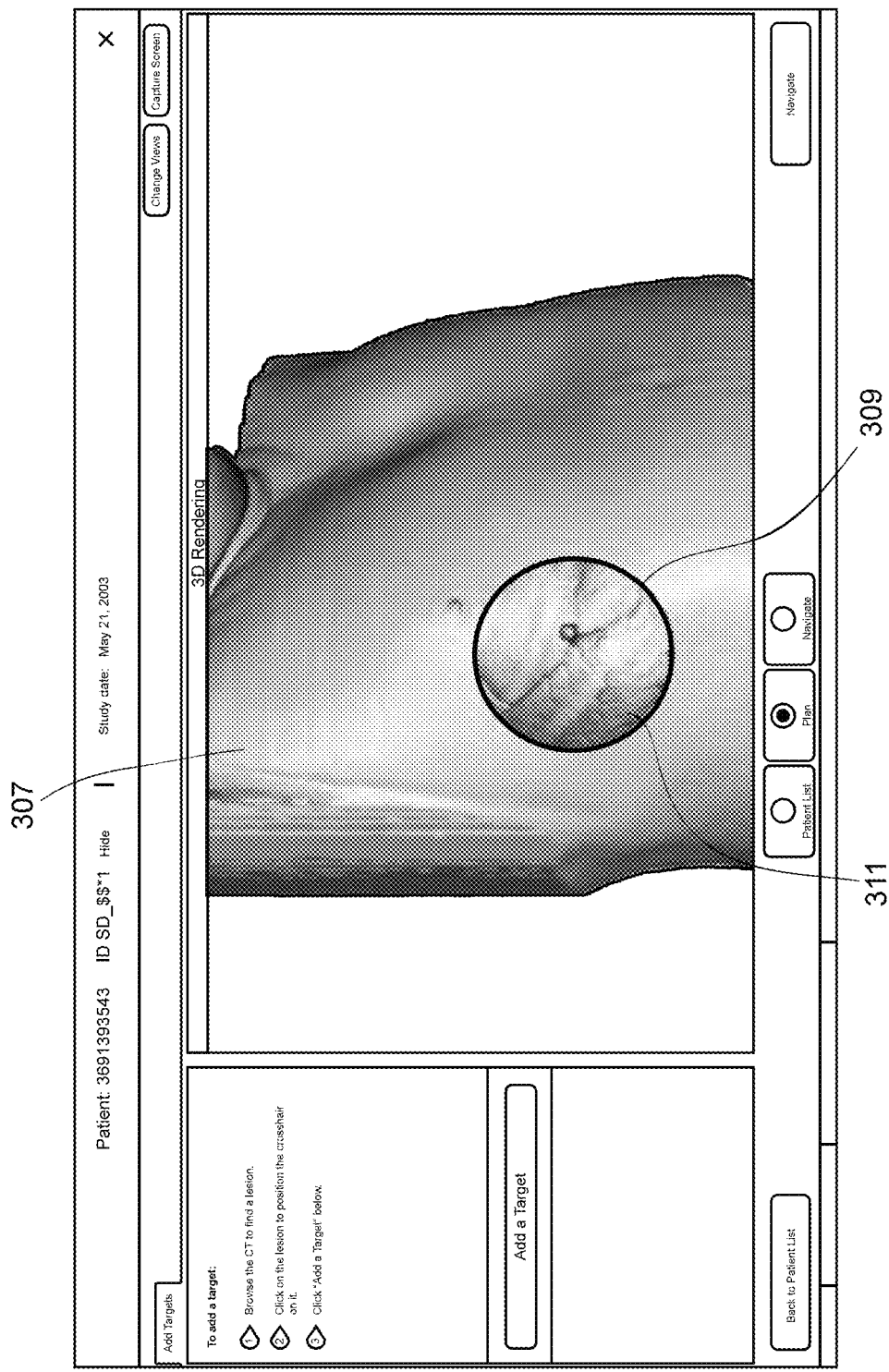
FIG. 11 is an illustration of a user interface presenting a view illustrating a representation of a patient's skin rendered over a 3D model and including a section of the skin peeled back or removed in an area of interest in accordance with an embodiment of the present disclosure.

For example, as shown in main view 294 of FIG. 9, the patient's chest is presented with 3D model 302 including a representation of the patient's skin 307 overlayed over the patient's rib cage 304 (FIG. 8) and other anatomical features 306 (FIG. 8) such that the end point 312 and the entry route marker 310 are shown exiting the representation of the patient's body. The end point 312 and the entry route marker 310 may also be presented as a representation of a surgical instrument 315, for example, an ablation needle, as shown in FIG. 10. By activating the change views button 313, all or a portion of the patient's skin 307 may be made at least partially transparent to present a clinician with a 3D model showing a relative position of the target ablation marker 308 (FIG. 8) and the end point 312 to the patient's skin 307. Adjusting the transparency of the patient's skin 307 allows the clinician to determine both where the entry route marker 310 enters the patient's skin and also the relative location of the entry route marker 310 to other anatomical features and critical structures once through the patient's skin. The clinician may also activate the change views button 313, activate a change view button bar 317 (FIG. 10), or the activate the 3D model directly to partially peel back, remove, or adjust each layer in a localized area 309 to reveal muscle 311, bone, lung 319 (FIG. 10), or other similar structures beneath the skin 307, as shown, for example, in FIG. 11. During lung or liver resection surgery planning, the lung 319 (FIG. 10) or liver may also include an indication or indicator of the treatment zone which presents a clinician with a visual representation of the portion of the lung 319 that is to be resected in the 3D model. The view 294 may also compute and provide an indication of the total volume of the target organ (lung, liver, etc.) and a quantification of the extent of the resection as compared to the total volume. The change views button 313 may also be activated to change the view presented in main view 294 between each of the views described above with respect to activating change views button 237 of view 230.

As shown in FIG. 8, details view 300 includes details about the target 314, treatment zone 316, and entry route 318. Target details 314 may include, for example, the width, height, depth, volume, and/or other parameters of the target as set during step S418. Treatment zone details 316 may include, for example, the diameter of the treatment zone, volume of the treatment zone, power level, duration, and other parameters related to the treatment zone set in step S420. Details relating to a selected instrument may also be included. Entry route details 318 may include, for example, the length from the end point 312 to the target treatment marker 308 along the entry route marker 310, and an angle of the entry route marker 310 relative to a fixed coordinate plane as set in S422. As shown in FIG. 6C, for example, the depth marker 285 may be set to determine the length from the tissue boundary 287 to the tip of the selected probe or needle 283.

During review of the treatment plan in view 292, the clinician may add additional routes in step S428 and may add additional targets in step S430 by selecting the add target tab 320 and returning to steps S424 and S416, respectively, or may review other treatment procedures which have been previously created by activating a respective target tab 322. In an embodiment, for example, as shown in FIG. 8, when a single target tab 322 is selected by the clinician, a target treatment marker 308 is presented in the 3D model 302 as described above. In an additional or alternative embodiment, the clinician may select or activate a common target tab or multiple target tabs 322 at the same time such that a target ablation marker 308 for each target tab 322 may be presented in the same 3D model 302 at the same time. This allows the clinician to compare the locations, sizes, and entry routes for each target in the same 3D model at the same time.

During review of the treatment plan in view 292, the clinician may activate an edit target details button 324 to return to view 244 and step S418 for modification of the target details. In view 292, the clinician may also select a delete target option 326 to delete the target and return to view 230 and step S416 to choose a new target.

If the clinician is satisfied with the treatment plan, the clinician may export the plan in step S423 for use during a surgical procedure by activating the export button 328. The plan may be exported to any form of non-transitory computer readable medium, memory or storage device as described above for memory 104 including, for example, a memory or storage on the device 100, a removable storage device, exported by transmission across a wired or wireless connection to a remote or server memory, etc.

The user interface module 202 may include a navigation bar 330, as shown in FIG. 3A which is activatable by the clinician to switch between various portions of user interface module 202. For example, as illustrated in FIG. 3A, the clinician may activate navigation bar 330 to switch between loading images, planning, and review. The navigation bar 330 may also include buttons which are activatable by the clinician to return the clinician to any previous steps or views of user interface module 202.

Each view of the user interface module 202 may include a toolbox 332 for controlling various parameters of the views and slices described above, as illustrated, for example, in FIG. 12. For example, toolbox 332 may include a zoom control 334 and a visual control 336. The clinician may activate the zoom control 334 to increase or decrease the zoom level of the particular view, slice, or image, in which the zoom control 334 resides. The clinician may also or alternatively activate the zoom control 334 to uniformly increase or decrease the zoom level of all of the views, slices, or images in a particular view at the same time. The zoom control 334 setting may also be carried over from view to view as the clinician progresses through the treatment planning steps described above.

Figure 12:
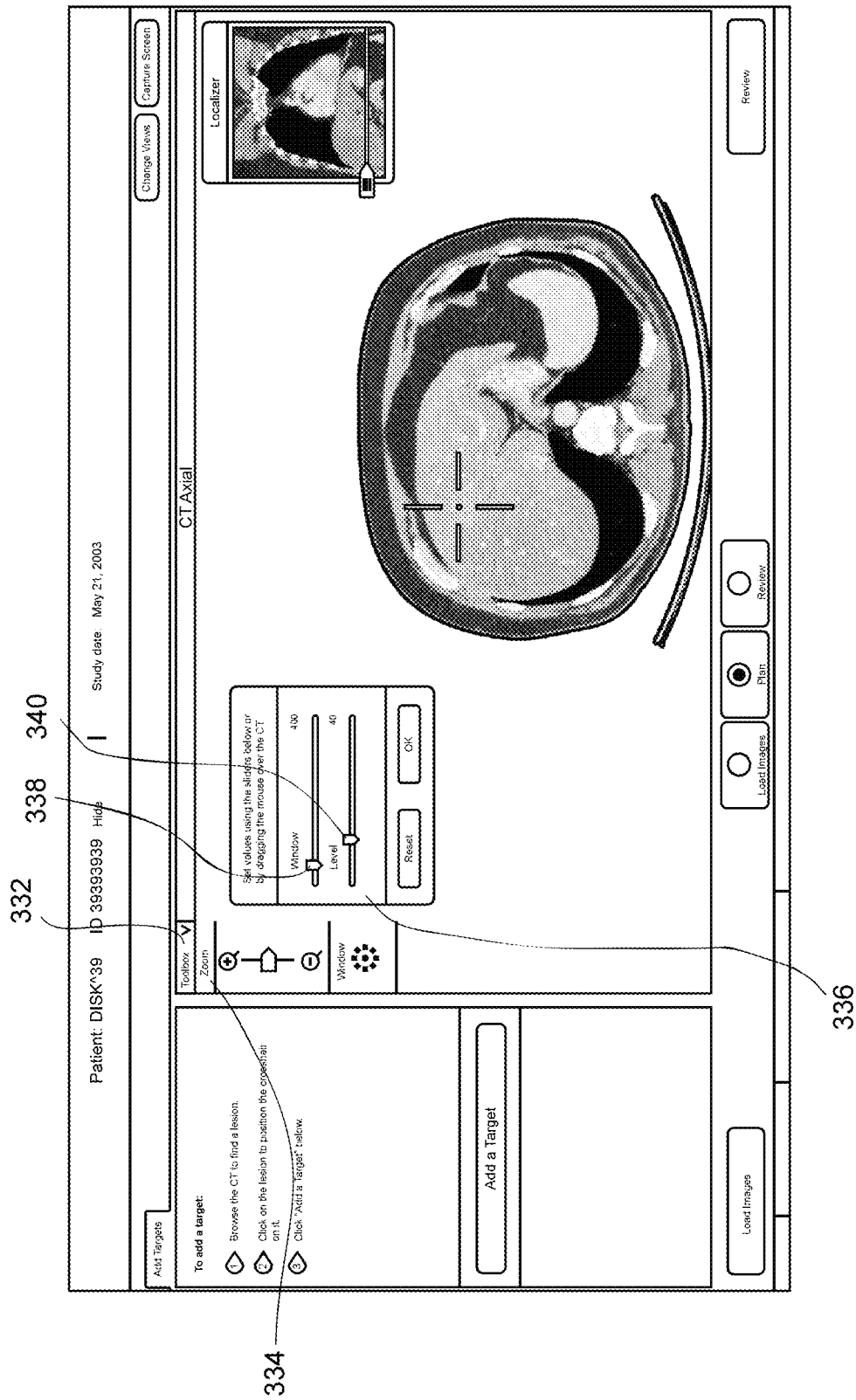
FIG. 12 is an illustration of a user interface presenting a view including a toolbox for adjusting display parameters of a slice of a 3D reconstruction presented in the view in accordance with an embodiment of the present disclosure.

Still referring to FIG. 12, visual control 336 includes a window slider 338 and a level slider 340. The clinician may activate the window slider 338 to control a contrast of a slice or image presented the particular window in which the visual control 336 resides while the level slider 340 may be activated by the clinician to control a brightness of a slice or image presented in the particular view where the visual control 336 resides. The clinician may also input a contrast or brightness value as desired. Alternatively or additionally, the clinician may activate visual control 336 to uniformly adjust the brightness and contrast of the slices or images in all of the slices or images in a particular view at the same time. The visual control 336 setting may also be carried over from view to view as the clinician progresses through the treatment planning steps described above. The visual control 336 settings may also be automatically configured depending on the type of treatment procedure being planned. For example, the visual control 336 settings may be set to preset values which provide a clinician with enhanced viewing of the patient's abdomen, airways, liver, lungs, pulmonary system, lung lesions, lung airways, or other similar patient features to allow the clinician to better identify potential targets. For example, each preset value may include an indicator corresponding to the particular part of the patient's anatomy to be examined.

Figure 13:
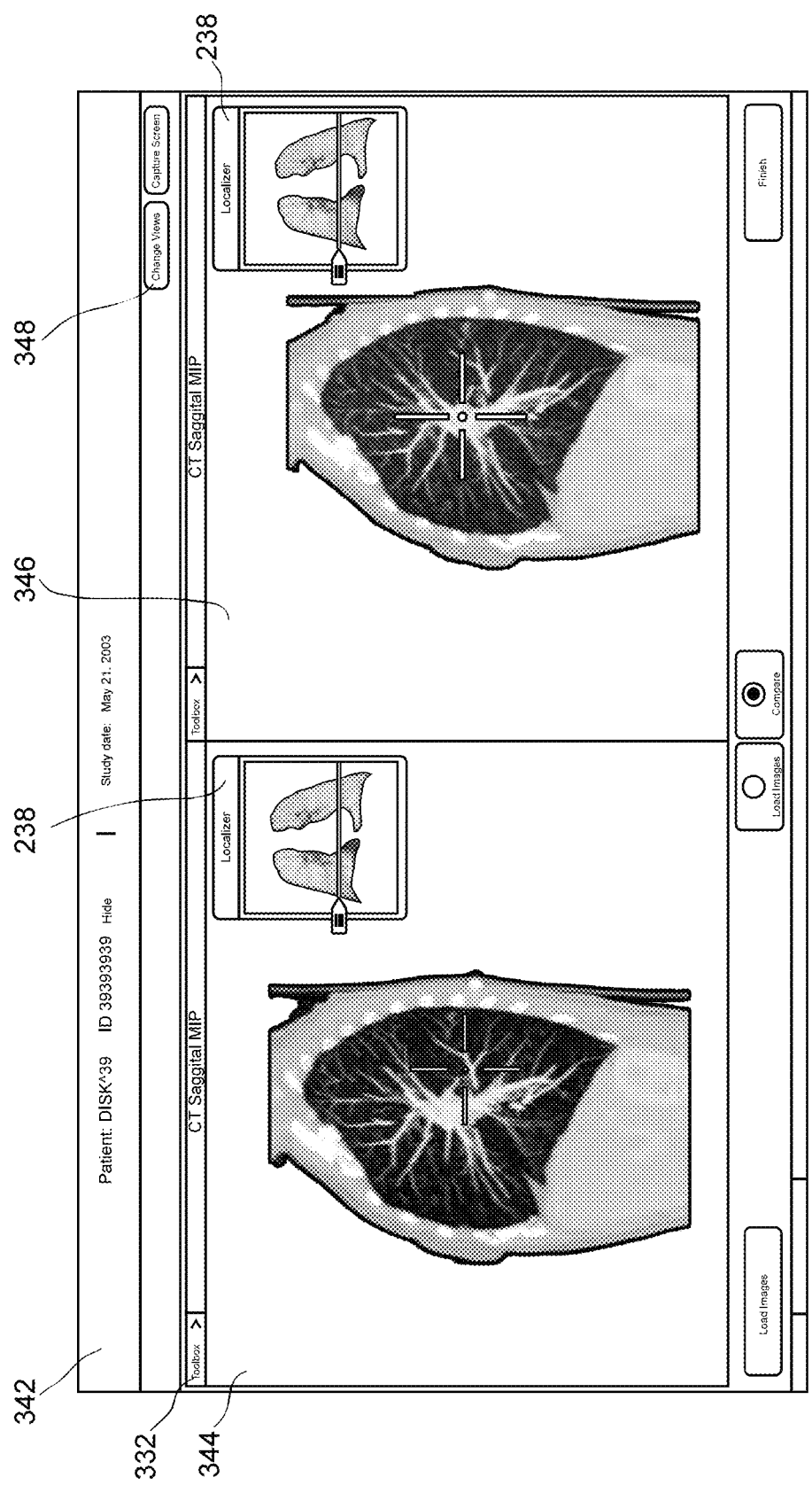
FIG. 13 is an illustration of a user interface presenting a view for comparing a pre-operative treatment plan to post-operative CT image data in accordance with an embodiment of the present disclosure.

After a treatment procedure has been completed, the clinician may wish to review the difference between the patient's pre-treatment CT image data and post-treatment CT image data. This may be beneficial where repeated treatments are necessary, for example where treatments must be made successively to avoid damaging particular structures such as blood vessels and the like. In an embodiment, treatment planning module 200 imports post-treatment CT image data in the manner described above for CT image data 220 and user interface module 202 opens a view 342 presenting a pre-treatment slice 344 and a post-treatment slice 346 for the clinician's review, as shown, for example, in FIG. 13. Pre-treatment slice 344 is an axial, coronal, or sagittal slice of a 3D reconstruction generated from the pre-treatment CT image data 220 while slice 346 is an axial, coronal, or sagittal slice of a 3D reconstruction generated from the newly imported post-treatment CT image data taken after the treatment procedure. Slices 344 and 346 are positioned in a side-by-side comparison so that a clinician may compare the pre-treatment plan and the post-treatment results to determine if the target has been effectively treated. Each of slices 344 and 346 includes a localizer 238 and tool box 332 as described above. Slices 344 and 346 may be independently manipulated by the clinician in the manner described above for slice 234 or alternatively may be linked together such that any manipulation performed on slice 344 by the clinician will be duplicated on slice 346 and vice versa. Slice 344 may also include a representation or indication of the location of the target to allow the clinician to easily find the target for comparison to slice 346. The clinician may also change the type of view presented in view 342 for each of slices 344 and 346 by activating a change views button 348 in a similar manner to activating change views button 237 (FIG. 4A) of view 230 as described above. For example, the clinician may activate the change views button 348 to change views between the axial, coronal, sagittal, MIP, 3D, or other similar views.

During any of the above described steps, the treatment planning module 200 may employ a variety of rendering and processing algorithms and techniques to isolate, identify, and/or render the CT image data 220 or the generated 3D reconstruction for presentation to the clinician. Segmentation is a type of processing algorithm that is typically applied to medical images in an attempt to define the boundaries of various types of tissue by comparing the values of each data element of the CT image data or the generated 3D reconstruction to a series of thresholds or other similar criteria. The segmentation algorithm groups together similar types of tissue, for example, lungs, airways, lung lobes, nodules, vessels, liver, ribs, heart, or other critical structures, based on the outcome of the comparison. Each group may then be separately processed for rendering and presentation to the clinician by the treatment planning module 200. For example, because the intensity of each pixel in a CT image is equivalent to an actual density of the tissue material that was scanned, segmentation may be used to separate tissue material having different densities by analyzing the intensity values in the CT image.

One benefit of segmentation is the ability to present each critical structure of the patient's anatomy to the clinician in visual form having a different color and/or transparency. This provides the clinician with an easy way of identifying different tissue types within the same image. For example, once segmented into groups, the lungs, airways, bones, etc. can each be presented with a different color or different transparency setting that may be adjustable by the clinician.

The treatment planning module 200 may utilize common techniques for segmentation including, for example, binary masking, determination of the optimum threshold that separates tissue and background, adaptive region growing, wavefront propagation, automatic or manual determination of seed points in the trachea, liver, or other critical structures, a fill holes algorithm for filling in holes in the binary mask by flood filling the background and inverting the result, a rolling ball algorithm to close the airways, blood vessels, and indentations corresponding to peripheral nodules, and a morphological closing operation.

The treatment planning module 200 may also segment tumors, either automatically or once identified by the clinician, from the surround tissue and present the clinician with the option to designate a seed point in an identified tumor. Using the seed point, treatment planning module 200 creates a region of interest around the seed point and searches for a threshold that results an object corresponding to the tumor. In this manner, an approximation of the boundaries of the tumor is mathematically determined based on the differences in the images on a voxel by voxel basis. This approximation can be implemented in the target identification steps described above. The segmented tumor may also be presented to the clinician as a 2D or 3D model which allows the clinician to determine the size and dimensions of the segmented tumor and the location of blood vessels or other similar features of interest in the segmented tumor.

As described above, treatment planning module 200 is configured to present a 3D model or representation of the patient's anatomy to the clinician. Treatment planning module 200 may utilize a variety of well-known 3D rendering processes or techniques to generate all or part the 3D model. For example, treatment planning module 200 may apply surface rendering to the 3D reconstruction or to a segmented portion of the 3D reconstruction to generate a 3D model or image for presentation to a clinician. During surface rendering, the treatment planning module 200 receives the 3D reconstruction and applies binary masks and various filters to the 3D reconstruction to generate a surface mesh. Examples of well-known filters used in surface rendering include dilation filters, masking filters, gaussian filters, and contour filters. Treatment planning module 200 may, for example, generate different kinds of 3D surface rendered images of a lung or another part of the patient's anatomy by using different combinations of filters and algorithms. In one example, the treatment planning module may apply a marching cubes algorithm to a segmentation of the lung to generate the 3D surface rendered image. In another example, the treatment planning module 200 may apply an image smoothing filter to the segmentation of the lung prior to applying the marching cubes algorithm to generate a 3D surface rendered image having a smoother surface. In yet another example, the treatment planning module 200 may use customized parameters on the segmentation of the lung or on the generated 3D surface rendered images to generate a surface rendered image having additional shine and smoothness. The level of shine and smoothness in the presented 3D surface rendered image may assist the clinician in identifying features on the outside surface of a lung or other structure that may be indicative of a potential target or area of interest.

The treatment planning module 200 is also configured to apply volume rendering to the 3D reconstruction or to a segmented portion of the 3D reconstruction to generate a 3D image for presentation to a clinician as is well known in the art. Volume rendered 3D images may show rough textures on the rendered surface which may assist a clinician in locating and identifying a target or area of interest on a surface of the 3D image. For example, the volume rendered 3D image may assist the clinician in identifying a diseased portion or an adhesion and may also be a useful tool for locating the peripheral nodules and potential targets of interest on the surface of a patient anatomy during the treatment planning procedure.

Treatment planning module 200 may also be configured to utilize both surface rendering and volume rendering at the same time to generate a 3D image for presentation to the clinician. For example, a skin surface may be surface rendered over a volume rendered 3D model. The transparency of skin surface may be adjusted at an area of interest to allow the volume rendered 3D model to be visible to the clinician. The clinician may utilize the 3D image during surgical treatment planning to determine, for example, a relative location of the target of interest to the patient's external anatomy, the location of the patient's ribs or other structures relative to the patient's external anatomy, potential locations for an access route to the target, potential locations for placement of an access portal, or other similar uses.

Treatment planning module 200 may also configured to simulate different states of the patient's anatomy in the 3D images. For example, the treatment planning module 200 may simulate the patient's left lung and right lung in both inflated and deflated states using a lung deflation algorithm. The lung deflation algorithm deforms one of the left and right lungs by using a thin-plate splines algorithm and leaves the trachea and the other lung unmodified. Anchor points may be provided where the deformed lung and bronchi connect to the trachea to provide for seamless deformation. The treatment planning module 200 may also simulate deflation of both the left lung and right lung simultaneously.

While the foregoing has been described and set forth with respect to determining medical treatment procedure including planning a route to a target within a patient, the same methodologies and systems may be employed to in a planning procedure to identify a target, a route to the target and to conduct a review of the proposed approach for treatment or servicing in other contexts, including without limitation analysis of piping systems, electronic systems, and other industrial applications where access to a target is limited and internal analyses of the system in question are required to ascertain the most desirable pathway to reach the target.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A system for planning a treatment procedure, the system comprising:
    a computing device including a memory and a processor; and
    a program stored in the memory that, when executed by the processor, causes the processor to present a user interface that guides a user through the planning of the treatment procedure, the user interface including:
    a treatment zone setting view presenting at least one slice of a 3D reconstruction generated from CT image data including a target,
    the treatment zone setting view further presenting a treatment zone marker defining a location and a size of a treatment zone,
    the treatment zone setting view configured to adjust the location and the size of the treatment zone defined by the treatment zone marker in response to received treatment zone marker adjustment user inputs,
    wherein the treatment zone setting view includes a 2D representation of an instrument,
    wherein in response to the received treatment zone marker adjustment user input an orientation and a position of the 2D representation of the instrument are adjusted relative to the at least one slice of the 3D reconstruction, and
    wherein the treatment zone setting view includes a user-selectable power level setting having a corresponding predetermined size limit, and an alert is generated when the size of the treatment zone defined by the treatment zone marker is adjusted to exceed the predetermined size limit corresponding to the user-selectable power level setting; and
    a volumetric view presenting a 3D rendering derived from the 3D reconstruction and a 3D representation of the treatment zone marker relative to structures depicted in the 3D rendering.

2. The system according to claim 1, wherein the 3D representation of the treatment zone marker in the volumetric view is a wireframe.

3. The system according to claim 1, wherein the 3D rendering is centered on one of the target, a target marker, the treatment zone marker, or a distal portion of the instrument.

4. The system according to claim 1, wherein the 3D rendering is rotatable in response to a received rotation user input.

5. The system according to claim 1, wherein the 3D rendering has a shape selected from the group consisting of a cubic shape, a rectangular shape, a pyramid shape, and a spherical shape.

6. The system according to claim 1, wherein the volumetric view further presents a 3D representation of the instrument, and wherein the adjustment of the orientation and the position of the 2D representation of the instrument in response to the received treatment zone marker adjustment user input in the treatment zone setting view also adjusts a corresponding orientation and position of the 3D representation of the instrument and the orientation and the position of the 3D representation of the treatment zone marker in the volumetric view.

7. The system according to claim 1, wherein the 2D representation of the instrument in the at least one slice of the treatment zone setting view includes a depth marker slidably disposed on the 2D representation of the instrument, the depth marker slidable to set a depth of insertion of the instrument in response to a received depth user input.

8. The system according to claim 1, wherein the treatment zone setting view includes a user-selectable needle setting having a corresponding predetermined size limit and an alert is generated when the size of the treatment zone defined by the treatment zone marker is adjusted to exceed the predetermined size limit corresponding to the user-selectable needle setting.

9. A non-transitory computer-readable storage medium encoded with a program that, when executed by a processor, performs the steps of
    presenting at least one slice of a 3D reconstruction generated from CT image data including a target in a treatment zone setting view;
    presenting a treatment zone marker defining a location and a size of a treatment zone on the at least one slice of the 3D reconstruction;
    adjusting the location and the size of the treatment zone defined by the treatment zone marker in response to received treatment zone marker adjustment user inputs, wherein the treatment zone setting view includes a 2D representation of an instrument, and
        wherein in response to the received treatment zone marker adjustment user input an orientation and a position of the 2D representation of the instrument are adjusted relative to the at least one slice of the 3D reconstruction;
    presenting a user-selectable power level setting having a corresponding predetermined size limit;
    generating an alert when the size of the treatment zone defined by the treatment zone marker is adjusted to exceed the predetermined size limit corresponding to the user-selectable power level setting;
    presenting a 3D rendering derived from the 3D reconstruction in a volumetric view; and
    presenting a 3D representation of the treatment zone marker relative to structures depicted in the 3D rendering in the volumetric view.

10. The non-transitory computer-readable storage medium according to claim 9, wherein the 3D representation of the treatment zone marker is a wireframe.

11. The non-transitory computer-readable storage medium according to claim 9, wherein the 3D rendering is centered on one of the target, a target marker, the treatment zone marker, or a distal portion of the instrument.

12. The non-transitory computer-readable storage medium according to claim 9, wherein the program is configured to rotate the 3D rendering in response to a received rotation user input.

13. The non-transitory computer-readable storage medium according to claim 9, wherein the 3D rendering has a shape selected from the group consisting of a cubic shape, a rectangular shape, a pyramid shape, and a spherical shape.

14. The non-transitory computer-readable storage medium according to claim 9, wherein the volumetric view further presents a 3D representation of the instrument, and wherein the adjustment of the orientation and the position of the 2D representation of the instrument in response to the received treatment zone marker adjustment user input in the treatment zone setting view also adjusts a corresponding orientation and position of the 3D representation of the instrument and the orientation and the position of the 3D representation of the treatment zone marker in the volumetric view.

15. The non-transitory computer-readable storage medium according to claim 9, wherein the 2D representation of the instrument in the at least one slice of the treatment zone setting view includes a depth marker slidably disposed on the 2D representation of the instrument, the depth marker slidable to set a depth of insertion of the instrument in response to a received depth user input.

16. The non-transitory computer-readable storage medium according to claim 9, wherein the program is configured to:
   present a user-selectable needle setting having a corresponding predetermined size limit; and
   generate an alert when the size of the treatment zone defined by the treatment zone marker is adjusted to exceed the predetermined size limit corresponding to the user-selectable needle setting.

* * * * *